United States Patent [19]

Finlayson et al.

[11] 4,412,018

[45] Oct. 25, 1983

[54] ORGANOPHILIC CLAY COMPLEXES, THEIR PREPARATION AND COMPOSITIONS COMPRISING SAID COMPLEXES

[75] Inventors: Claude M. Finlayson, Houston, Tex.; Wilbur S. Mardis, Trenton, N.J.

[73] Assignee: NL Industries, Inc., New York, N.Y.

[21] Appl. No.: 207,542

[22] Filed: Nov. 17, 1980

[51] Int. Cl.³ .................... B01J 13/00; C08K 9/04
[52] U.S. Cl. ................ 523/508; 106/287.25; 106/287.3; 252/28; 252/309; 252/315.2; 260/448 C; 524/445
[58] Field of Search ............. 260/448 C; 252/316, 252/309 B, 8.5 P, 28; 523/508

[56] References Cited

U.S. PATENT DOCUMENTS

| | | |
|---|---|---|
| 2,355,356 | 5/1941 | Young . |
| 2,531,427 | 11/1950 | Hauser ................. 252/309 X |
| 2,531,440 | 11/1950 | Jordan . |
| 2,548,679 | 5/1951 | Olin . |
| 2,739,067 | 3/1956 | Ratcliffe . |
| 2,750,296 | 6/1956 | Curado et al. . |
| 2,754,219 | 7/1956 | Voet et al. . |
| 2,775,617 | 12/1956 | Shapiro et al. . |
| 2,859,234 | 11/1958 | Clem ......................... 260/448 C |
| 2,885,360 | 5/1959 | Haden et al. . |
| 3,136,819 | 6/1954 | Shapiro et al. . |
| 3,461,163 | 8/1969 | Boothe . |
| 3,472,740 | 10/1969 | Boothe . |
| 3,537,994 | 11/1970 | House . |
| 3,929,849 | 12/1975 | Oswald . |
| 3,945,836 | 3/1976 | Miyata . |
| 4,054,537 | 10/1977 | Wright et al. ............ 252/316 X |
| 4,097,437 | 1/1978 | Dhake . |
| 4,105,578 | 8/1978 | Finlayson et al. .......... 252/316 |
| 4,193,806 | 3/1980 | Finlayson . |
| 4,208,218 | 6/1980 | Finlayson ................ 252/316 X |
| 4,216,135 | 8/1980 | Finlayson ................ 252/316 X |
| 4,317,737 | 3/1982 | Oswald . |

*Primary Examiner*—Richard D. Lovering

[57] ABSTRACT

An organophilic clay gellant and methods of using and making the same which comprises the reaction product of an organic cation, an organic anion and a smectite-type clay having a cation exchange capacity of at least 75 milliequivalents per 100 grams of said clay such that an organic cation-organic anion complex is intercalated with the smectite-type clay and the cation exchange sites of the smectite-type clay are substituted with the organic cation.

24 Claims, 4 Drawing Figures

ORGANOPHILIC CLAY COMPLEXES, THEIR PREPARATION AND COMPOSITIONS COMPRISING SAID COMPLEXES

This invention relates to organophilic organic-clay complexes which are dispersible in organic liquids to form a gel therein. Depending on the composition of the gel, such gels may be useful as lubricating greases, oil base muds, oil base packer fluids, paint-varnish-lacquer removers, paints, foundry molding sand binders, adhesives and sealants, inks, polyester laminating resins, polyester gel coats, and the like.

It is well known that the organic compounds which contain a cation will react under favorable conditions by ion-exchange with clays which contain a negative layer-lattice and exchangeable cations to form organophilic organic-clay products. If the organic cation contains at least one alkyl group containing at least 10 carbon atoms, then such organoclays have the property of swelling in certain organic liquids. See for Example U.S. Pat. No. 2,531,427 and U.S. Pat. No. 2,966,506, both incorporated herein by reference, and the book "Clay Mineralogy", 2nd Edition, 1968 by Ralph E. Grim (McGraw Hill Book Co., Inc.), particularly Chapter 10, Clay-Mineral-Organic Reactions; pp. 356–368—Ionic Reactions, Smectite; and pp. 392-401—Organophilic Clay-Mineral Complexes.

It is also known that organic compounds presented in the anionic form are usually repelled by, rather than attracted to, the negatively charged clay surface. This effect is referred to as negative adsorption. However, positive adsorption of anions can occur under conditions in which such compounds exist in the molecular, i.e. undissociated form. See "Chemistry of Clay-Organic Reactions" 1974 by B. K. G. Theng, John Wiley & Sons.

In contrast, Wada found that this phenomena, i.e. adsorption, does occur with certain ionic compounds when reacted with halloysite, kaolinite group material, to form intersalates. Intersalation was achieved by grinding the mineral with moist crystals of salts of low molecular weight carboxylic acids or by contacting the mineral with saturated solutions. This interlayer complex contained the complete salt as well as water. The intersalated material however was removed by washing with water resulting in either hydration of the interlayer or collapse to the original spacing. No evidence of variation in basal spacing was found with montmorillonite treated with salts in contrast with halloysite. See *The American Mineralogist*, Volume 44, 1959, by K. Wada "Oriented Penetration of Ionic Compounds between the Silicate Layers of Halloysite".

Since the commercial introduction of organoclays in the early 1950's, it has become well known that maximum gelling (thickening) efficiency from these organoclays is achieved by adding a low molecular weight polar organic material to the composition. Such polar organic materials have been various called dispersants, dispersion aids, solvating agents, dispersion agents and the like. See for example the following U.S. Pat. Nos.: O'Halloran 2,677,661; McCarthy et al. 2,704,276; Stratton 2,833,720; Stratton 2,879,229; Stansfield et al. 3,294,683. The use of such dispersion aids was found unnecessary when using specially designed organophilic clays derived from substituted quaternary ammonium compounds. See U.S. Pat. Nos.: Finlayson et al. 4,105,578 and Finlayson 4,208,218.

In contrast to the prior art organoclay compositions, a self-activating rheological agent has been unexpectedly produced which does not require the addition of polar solvent activators, which agent is produced from the reaction of an organic cation, organic anion and smectite-type clay.

An organophilic clay gellant having enhanced dispersibility in non-aqueous systems and process for making and using the same has been unexpectedly discovered which comprises the reaction product of an organic cation, an organic anion and a smectite-type clay having a cation exchange capacity of at least 75 milliequivalents per 100 grams of said clay such that an organic cation-organic anion complex is intercalated with the smectite-type clay and the cation exchange sites of the smectite-type clay are substituted with the organic cation.

FIGS. 1, 2, 3 and 4 show the basal plan spacing diffraction patterns of various clay reaction products.

The clays used to prepare the organophilic clay gellants of this invention are smectite-type clays which have a cation exchange capacity of at least 75 milliequivalents per 100 grams of clay. Particularly desirable type of clay are the naturally-occurring Wyoming varieties of swelling bentonites and like clays and hectorite, a swelling magnesium-lithium silicate clay.

The clays, especially the bentonite type clays, are preferably converted to the sodium form if they are not already in this form. This can conveniently be done by preparing an aqueous clay slurry and passing the slurry through a bed of cation exchange resin in the sodium form. Alternatively, the clay can be mixed with water and a soluble sodium compound such as sodium carbonate, sodium hydroxide and the like, followed by shearing the mixture with a pugmill or extruder.

Smectite-type clays prepared naturally or synthetically by either a pneumatolytic or, preferably a hydrothermal synthesis process can also be used to prepare the present organophilic clays. Representative of such clays are montmorillonite, bentonite, beidellite, hectorite, saponite, and stevensite. These clays may be synthesized hydrothermally by forming an aqueous reaction mixture in the form of a slurry containing mixed hydrous oxides or hydroxides of the desired metal with or without, as the case may be, sodium (or alternate exchangeable cation of mixture thereof) fluoride in the proportions for the particular synthetic smectite desired. The slurry is then placed in an autoclave and heated under autogenous pressure to a temperature within the range of approximately 100° to 325° C., preferably 274° to 300° C., for a sufficient period of time to form the desired product.

The cation exchange capacity of the smectite-type clays can be determined by the well-known ammonium acetate method.

The organic cationic compounds which are useful in this invention may be selected from a wide range of materials that are capable of forming an organophilic clay by exchange of cations with the smectite-type clay. The organic cationic compound must have a positive charge localized on a single atom or on a small group of atoms within the compound. Preferably the organic cation is selected from the group consisting of quaternary ammonium salts, phosphonium salts, sulfonium salts and mixtures thereof wherein the organic cation contains at least one lineal or branched alkyl group having 12 to 22 carbon atoms. The remaining moieties on the central positively charged atoms are chosen from (a) lineal or branched alkyl groups having 1 to 22 carbon atoms; (b) aralkyl groups, that is benzyl and substituted benzyl moieties including fused ring moieties having lineal or branched 1 to 22 carbon atoms in the alkyl portion of the structure; (c) aryl groups such as phenyl and substituted phenyl including fused ring aromatic substituents; and (d) hydrogen.

The long chain alkyl radicals containing at least one group having 12 to 22 carbon atoms may be derived from natural occurring oils including various vegetable oils, such as corn oil, coconut oil, soybean oil, cottonseed oil, castor oil and the like, as well as various animal oils or fats such as tallow oil. The alkyl radicals may likewise be petrochemically derived such as from alpha olefins. Additional exemplary radicals include methyl, ethyl, decyl, lauryl, stearyl.

Additional examples of aralkyl, that is benzyl and substituted benzyl moieties would include those materials derived from, e.g. benzyl halides, benzhydryl halides, trityl halides, α-halo-α-phenylalkanes wherein the alkyl chain has from 1 to 22 carbon atoms such as 1-halo-1-phenylethane, 1-halo-1-phenyl propane, and 1-halo-1-phenyloctadecane; substituted benzyl moieties such as would be derived from ortho, meta and para-chlorobenzyl halides, para-methoxybenzyl halides, ortho, meta and para-nitrilobenzyl halides, and ortho, meta and para-alkylbenzyl halides wherein the alkyl chain contains from 1 to 22 carbon atoms; and fused ring benzyl-type moieties such as would be derived from 2-halomethylnaphthalene, 9-halomethylanthracene and 9-halomethylphenanthrene, wherein the halo group would be defined as chloro, bromo, iodo, or any other such group which serves as a leaving group in the nucleophilic attack of the benzyl type moiety such that the nucleophile replaces the leaving group on the benzyl type moiety.

Examples of aryl groups would include phenyl such as in N-alkyl and N,N-dialkyl anilines, wherein the alkyl groups contain between 1 and 22 carbon atoms; ortho, meta and para-nitrophenyl, ortho, meta and para-alkyl phenyl, wherein the alkyl group contains between 1 and 22 carbon atoms, 2-, 3-, and 4-halophenyl wherein the halo group is defined as chloro, bromo, or iodo, and 2-, 3-, and 4-carboxyphenyl and esters thereof, where the alcohol of the ester is derived from an alkyl alcohol, wherein the alkyl group contains between 1 and 22 carbon atoms, aryl such as a phenol, or aralkyl such as benzyl alcohols; fused ring aryl moieties such as naphthalene, anthracene, and phenanthrene.

Many processes are known to prepare organic cationic salts. For example when preparing a quaternary ammonium salt one skilled in the art would prepare a dialkyl secondary amine, for example, by the hydrogenation of nitriles, see U.S. Pat. No. 2,355,356; form the methyl dialkyl tertiary amine by reductive alkylation using formaldehyde as the source of methyl radical. Also see Shapiro et al. U.S. Pat. No. 3,136,819 for forming the quaternary amine halide by adding benzyl chloride or benzyl bromide to the tertiary amine as well as Shapiro et al. U.S. Pat. No. 2,775,617. The salt anion is preferably selected from the group consisting of chloride and bromide, and mixtures thereof, and is more preferably chloride, although other anions such as acetate, hydroxide, nitrite, etc., may be present in the organic cationic compound to neutralize the cation.

These organic cationic compounds can be represented by the formulae:

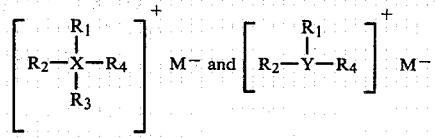

wherein X is nitrogen or phosphorus, Y is sulfur, $M^-$ is selected from the group consisting of chloride, bromide, iodide, nitrite, hydroxide, acetate, methyl sulfate, and mixtures thereof; and wherein $R_1$ is an alkyl group having 12 to 22 carbon atoms; and wherein $R_2$, $R_3$ and $R_4$ are selected from the group consisting of hydrogen; alkyl groups containing 1 to 22 carbon atoms; aryl groups; aralkyl groups containing 1 to 22 carbon atoms on the alkyl chain, and mixtures thereof.

The organic anions useful in this invention may be selected from a wide range of materials providing they are capable of reacting with an organic cation and form intercalations with a smectite-type clay as an organic cation-organic anion complex. The molecular weight (gram molecular weight) of the organic anion is preferably 3,000 or less, and most preferably 1,000 or less and contains at least one acidic moiety per molecule as disclosed herein. The organic anion is preferably derived from an organic having a $pK_A$ less than about 11.0. As indicated, the source acid must contain at least one ionizable hydrogen having the preferred $pK_A$ in order to allow the formation of the organic cation-organic anion complex and subsequent intercalation reaction to occur.

Also useable is any compound which will provide the desired organic anion on hydrolysis. Representative compounds include:
(1) acid anhydrides including acetic anhydride, maleic anhydride, succinic anhydride and phthalic anhydride;
(2) acid halides including acetylchloride octanoyl chloride, lauroyl chloride, lauroyl bromide and benzoyl bromide;
(3) 1,1,1-trihalides including 1,1,1-trichloroethane and 1,1,1-tribromooctane; and
(4) orthoesters including ethylorthoformate, and ethylorthostearate.

The organic anions may be in the acid or salt form. Salts may be selected from alkali metal salts, alkaline earth salts, ammonia, and organic amines. Representative salts include: hydrogen, lithium, sodium, potassium, magnesium, calcium, barium, ammonium and organic amines such as ethanolamine, diethanolamine, triethanolamine, methyl diethanolamine, butyl diethanolamine, diethyl amine, dimethyl amine, triethyl amine, dibutyl amine, and so forth, and mixtures thereof. The most preferred salt is sodium as the alkali metal salt.

Exemplary types of suitable acidic functional organic compounds useful in this invention include:
(1) Carboxylic acids including:
  (a) benzene carboxylic acids such as benzoic acid, ortho, meta and para-phthalic acid, 1,2,3-benzene tricarboxylic acid; 1,2,4-benzene tricarboxylic acid; 1,3,5-benzenetricarboxylic acid; 1,2,4,5-benzene tetracarboxylic acid; 1,2,3,4,5,6-benzene hexacarboxylic acid (mellitic acid);
  (b) alkyl carboxylic acids having the formula H-$(CH_2)_n$—COOH, wherein n is a number from 1 to 20, such compounds include acetic acid; propionic acid; butanoic acid; pentanoic acid; hexanoic acid;

heptanoic acid; octanoic acid; nonanoic acid; decanoic acid; undecanoic acid; lauric acid; tridecanoic acid; tetradecanoic acid; pentadecanoic acid; hexadecanoic acid; heptadecanoic acid; octadecanoic acid (stearic acid); nonadecanoic acid; eicosonic acid.

(c) alkyl dicarboxylic acids having the formula HOOC-(CH$_2$)n—COOH, wherein n is 1 to 8 such as oxalic acid; malonic acid; succinic acid; glutaric acid; adipic acid; pimelic acid; suberic acid; azelaic acid; sebacic acid;

(d) hydroxyalkyl carboxylic acids such as citric acid; tartaric acids; malic acid; mandelic acid; and 12-hydroxystearic acid;

(e) unsaturated alkyl carboxylic acids such as maleic acid; fumaric acid; and cinnamic acid;

(f) fused ring aromatic carboxylic acids such as naphthalenic acid; and anthracene carboxylic acid;

(g) cycloaliphatic acids such as cyclohexane carboxylic acid; cyclopentane carboxylic acid; furan carboxylic acids.

(2) Organic sulfuric acids including:
(a) sulfonic acids including:
(1) benzene sulfonic acids such as benzene sulfonic acid; phenol sulfonic acid; dodecylbenzene sulfonic acid; benzene disulfonic acid, benzene trisulfonic acids; para-toluene sulfonic acid; and
(2) alkyl sulfonic acids such as methane sulfonic acid; ethane sulfonic acid; butane sulfonic acid; butane disulfonic acid; sulfosuccinate alkyl esters such as dioctyl succinyl sulfonic acid; and alkyl polyethoxy-succinyl sulfonic acid; and
(b) alkyl sulfates such as the lauryl half ester of sulfuric acid and the octadecyl half ester of sulfuric acid.

(3) Organophosphorus acids including:
(a) phosphonic acids have the formula:

wherein R is an aryl group or alkyl having 1 to 22 carbon atoms;
(b) phosphinic acids having the formula:

wherein R is an aryl group or alkyl group having 1 to 22 carbon atoms, such as dicyclohexyl phosphinic acid; dibutyl phosphinic acid; and dilauryl phosphinic acid;
(c) thiophosphinic acids having the formula:

wherein R is an aryl group or alkyl group having 1 to 22 carbon atoms such as di-iso-butyl dithiophosphinic acid; dibutyl dithiophosphinic acid; dioctadecyl dithiophosphinic acid;
(d) phosphites, that is diesters of phosphorous acid having the formula: HO-P(OR)$_2$ wherein R is an alkyl group having 1 to 22 carbon atoms such as dioctadecylphosphite;

(e) phosphates, that is diesters of phosphoric acid having the formula:

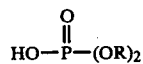

wherein R is an alkyl group having 1 to 22 carbon atoms, such as dioctadecyl phosphate.

(4) Phenols such as phenol; hydroquinone; t-butylcatechol; p-methoxyphenol; and naphthols.

(5) thioacids having the formula:

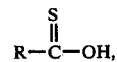

and

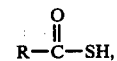

and

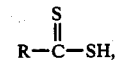

wherein R is an aryl group or alkyl group having 1 to 22 carbon atoms, such as thiosalicylic acid; thiobenzoic acid; thioacetic acid; thiolauric acid; and thiostearic acid.

(6) Amino acids such as the naturally occurring amino acids and derivatives thereof such as 6-aminohexanoic acid; 12-aminododecanoic acid; N-phenylglycine; and 3-aminocrotonoic acid.

(7) Polymeric acids prepared from acidic monomers wherein the acidic function remains in the polymer chain such as low molecular weight acrylic acid polymers and copolymers; styrene maleic anhydride copolymers.

(8) Miscellaneous acids and acid salts such as ferrocyanide; ferricyanide; sodium tetraphenylborate; phosphotungstic acid; phosphosilicic acid, or any other such anion which will form a tight ion pair with an organic cation, i.e., any such anion which forms a water insoluble precipitate with an organic cation.

The organophilic clays of this invention can be prepared by admixing the clay, organic cation, organic anion and water together, preferably at a temperature within the range from 20° C. to 100° C., more preferably 60° C. to 77° C. for a period of time sufficient for the organic cation and organic anion complex to intercalate with the clay particles, followed by filtering, washing, drying and grinding. The addition of the organic cation and organic anion may be done either separately or as a complex. In using the organophilic clays in emulsions, the drying and grinding steps may be eliminated. When admixing the clay, organic cation, organic anion and water together in such concentrations that a slurry is not formed, then the filtration and washing steps can be eliminated.

The clay is preferably dispersed in water at a concentration from about 1 to 80% and preferably 2% to 7%, the slurry optionally centrifuged to remove non-clay impurities which constitute about 10% to about 50% of the starting clay composition, the slurry agitated and heated to a temperature in the range from 60° C. to 77° C.

The organophilic clays of the invention may be prepared by admixing the organic anion with a clay and water together, preferably at a temperature between 20° C. and 100° C. for a sufficient time to prepare a homogenous mixture followed by the addition of the organic cation in sufficient amounts to satisfy the cation exchange capacity of the clay and the cationic capacity of the organic anion. The mixture is reached with agitation at a temperature between 20° C. and 100° C. for a sufficient time to allow the formation of an organic cation-organic anion complex which is intercalated with the clay and the cation exchange sites of the clay are substituted with the organic cation. Reaction temperatures below 20° C. or above 100° C. while useable are not preferred because of the need for additional processing apparatus, namely cooling devices and pressure reactors.

The amount of organic anion added to the clay for purposes of this invention must be sufficient to impart to the organophilic clay the enhanced dispersion characteristic desired. This amount is defined as the milliequivalent ratio which is the number of milliequivalents (M.E.) of the organic anion in the organoclay per 100 grams of clay, 100% active clay basis. The organophilic clays of this invention must have an anion milliequivalent ratio of 5 to 100 and preferably 10 to 50. At lower anion milliequivalent ratios the enhanced dispersibility and efficiency of the organophilic clays are negligible. At higher anion M.E. ratios the efficiency of the organophilic clay reaction product is reduced from nonintercalated organic cation-organic anion complexes or ion pairs.

The organic anion is preferably added to the reactants in the desired milliequivalent ratio as a solid or solution in water under agitation to effect a macroscopically homogenous mixture.

The organic cation is employed in a sufficient quantity to at least satisfy the cation exchange capacity of the clay and the cationic activity of the organic anion. Additional cation above the sum of the exchange capacity of the clay and anion may be optionally used. It has been found when using the smectite-type clays of this invention that use of at least 90 milliequivalents of organic cation is sufficient to satisfy at least a portion of the total organic cation requirement. Use of amounts from 80 to 200 M.E., and preferably 100 to 160 M.E. are acceptable. At lower milliequivalents ratios incomplete reaction between the organic cation and clay or organic anion will occur resulting in the formation of ineffective gellants.

For convenience of handling it is preferred that the total organic content of the organophilic clay reaction products of this invention should be less than about 50% by weight of the organoclay. While higher amounts are usable the reaction product is difficult to filter, dry and grind.

A preferred process for preparing an organophilic clay gellant may be described more particularly which involves:
(a) preparing a slurry of smectite-type clay in water at 1 to 80% by weight of said clay;
(b) heating the slurry to a temperature between 20° C. and 100° C.;
(c) adding 5 to 100 milliequivalents of an organic anion per 100 grams of clay, 100% active clay basis and an organic cation in a sufficient amount to satisfy the cation exchange capacity of the smectite-type clay and the cationic activity of the organic anion while agitating the reaction solution;
(d) continuing the reaction for a sufficient time to form a reaction product comprising an organic cation-organic anion complex which is intercalated with the smectite-type clay and the cation exchange sites of the smectite-type clay are substituted with the organic cation; and
(e) recovering the reaction product.

The compositions of the invention as discussed above find wide utility as rheological additives in non-aqueous fluid systems generally.

The attached illustrations demonstrate the effect of various organic additive treatments upon the basal plane spacing present in smectite-type clays of this invention and notably the sodium form of Wyoming bentonite. These illustrations are X-ray diffraction patterns of anion treated clay products from which the clay has been removed from the solvent (water) used in its preparation. The X-ray diffraction patterns were performed on a X-ray diffractometer. The figures depict the diffraction intensity versus basal plane spacings measured in Angstroms.

Figure 1:
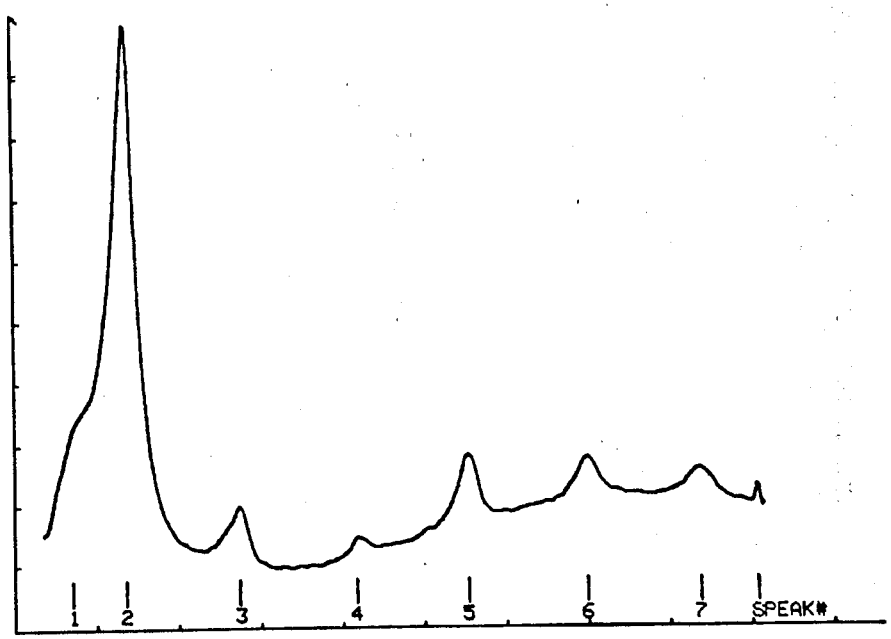
FIG. 1 shows the diffraction pattern of a conventional organophilic clay prepared from benzyl dimethyl hydrogenated tallow ammonium bentonite having an M.E. of 102.
Figure 2:
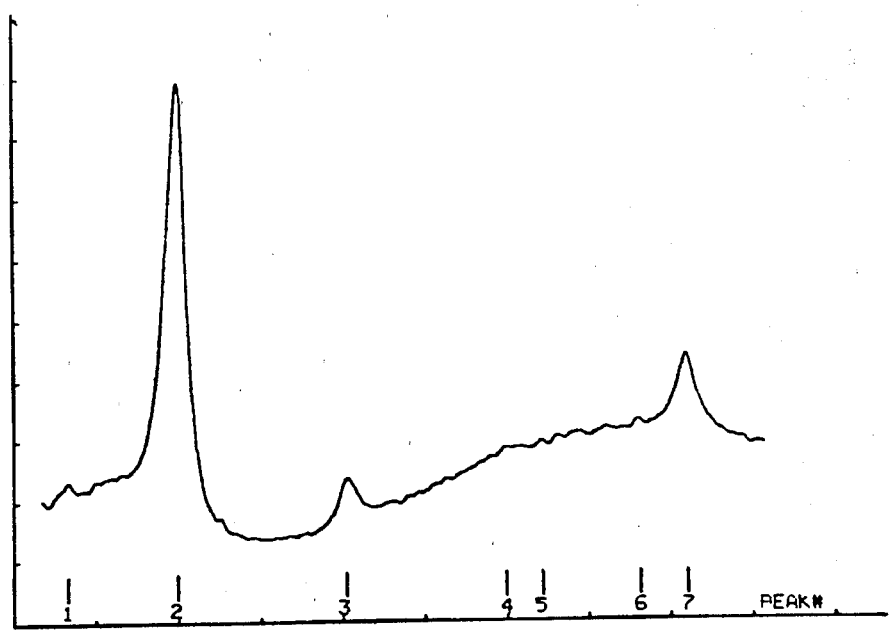
FIG. 2 shows the diffraction pattern of a sodium bentonite clay treated with 60 milliequivalents of sodium dioctyl sulfosuccinate.
Figure 3:
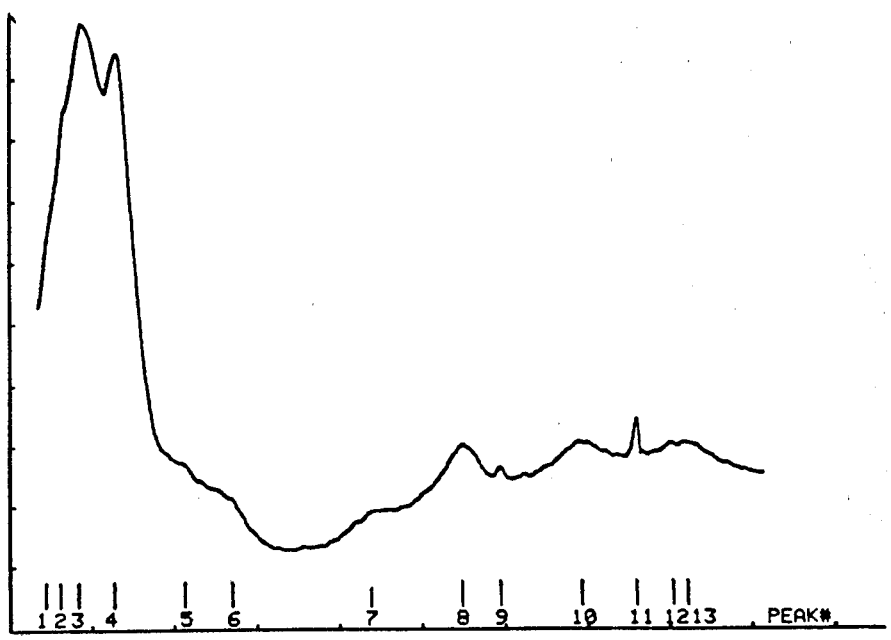
FIG. 3 shows the diffraction pattern of an inventive organophilic clay prepared from sodium bentonite treated with 22.5 milliequivalents of sodium benzoate, followed by 122.5 milliequivalents of benzyl dimethyl hydrogenated tallow ammonium chloride per 100 grams of clay, 100% active clay basis.
Figure 4:
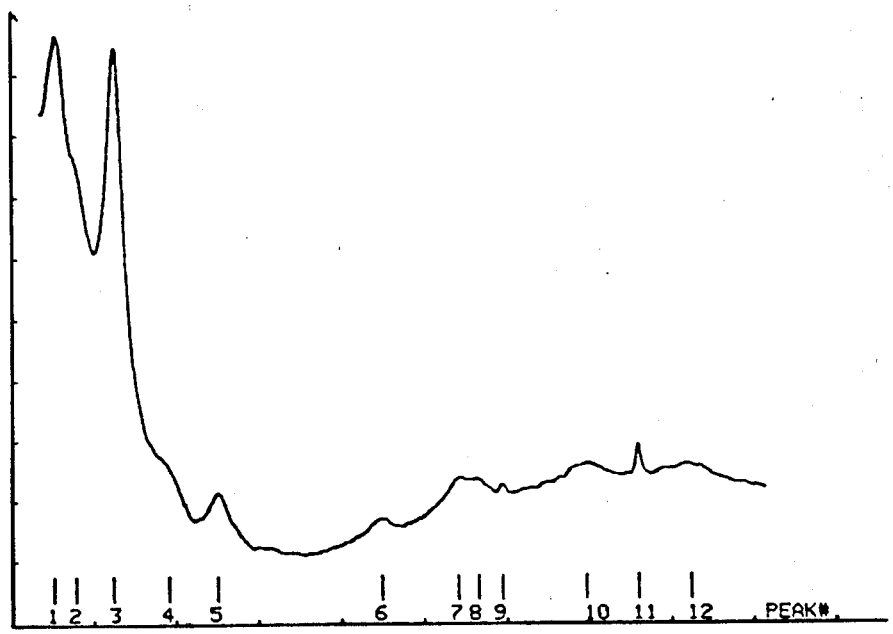
FIG. 4 shows the diffraction pattern of an inventive organophilic clay prepared from sodium bentonite treated with 22.5 milliequivalents of sodium laurylsulfate followed by 122.5 milliequivalents of benzyl dimethyl hydrogenated tallow ammonium chloride per 100 grams of clay, 100% active clay basis.

The illustrations clearly demonstrate the formation of organophilic clays by this invention to have increased basal plane spacings over conventionally prepared materials and that the mere reaction with an anion does not result in the formation of a reaction product. Note the spacings present in the figures notably FIG. 1 at 18.6 Å, FIG. 2 at 12.7 Å with 12.6 Å inherently present in the sodium bentonite clay, FIG. 3 at 29.97 Å and FIG. 4 at 48.63 Å and 32.21 Å.

The non-aqueous fluid compositions in which the self activating organophilic clays are useful include paints, varnishes, enamels, waxes, epoxies, mastics, adhesives, cosmetics, inks, polyester laminating resins and polyester gel coats, and the like. These fluids may be prepared by any conventional method such as described in U.S. Pat. No. 4,208,218 including colloid mills, roller mills, ball mills, and high speed dispersers, in which the fluid pigment materials become well dispersed in the organic vehicle by the high shear used in processing.

The organophilic clay gellant is employed in such compositions in amounts sufficient to obtain the desired rheological properties such as high viscosity at low shear rates, control of sagging of fluid films and prevention of settling and hard packing of pigments present in the non-aqueous fluid compositions. Amounts of the organophilic clay gellant employed in the non-aqueous fluid system should preferably be between about 0.1% and about 10% based on the weight of the treated non-aqueous fluid system and preferably between 0.3% and 5.0% to yield the desired rheological effects.

The following examples are given to illustrate the invention, but are not deemed to be limiting thereof. All percentages given throughout the specification are based upon weight unless otherwise indicated.

A simple convenient test has been devised to illustrate the enhanced dispersion characteristics of the organophilic clays utilized in this invention and exemplified in the following Examples to show the results potentially obtainable in utilizing the compositions of this invention. The test is called the solvent compatibility test. The solvent compatibility test is conducted by taking a sample of the organophilic clay which is sifted into 10 milliliters of various solvents contained in separate 10 milliliter graduated cylinders. The organophilic clay is added at such a rate that the particles are wetted evenly and clumping is not permitted to occur. The samples are allowed to equilibrate after all the organophilic clay has been added (approximately 30 minutes). The volume occupied by the organophilic clay is then recorded in tenths of a milliliter; this number is called the swelling volume.

The mixture is vigorously shaken 50 times, 10 times horizontally, 40 times vertically, and allowed to stand overnight. The volume occupied by the organophilic clay is again recorded in tenths of a milliliter; this value is called the settling volume.

The swelling volume gives an indication of the compatibility of the organic portion of the organphilic clay with the solvents tested; the settling volume gives an indication of the ease of dispersion of the organophilic clay in that solvent under low shear conditions.

Because of variances in the rate of sifting of the organoclay into the solvent and the vigor with which the sample is shaken, the number are not absolute. Small differences in the volumes are not considered significant, rather, the values are intended to be for comparison only.

EXAMPLES 1 to 7

These Examples demonstrate various methods for preparing the organophilic clays of this invention.

A container of suitable size was charged with a 3% clay slurry (sodium form of Wyoming bentonite) and the slurry was heated to 60° C. with stirring. According to the methods of addition described below, a solution of the organic anionic compound and/or organic cationic compound is added to the clay slurry and stirred for a period of time sufficient to complete the reaction (generally 10 to 60 minutes). The organoclay is collected on a vacuum filter. The filter cake is washed with hot (40°-80° C.) water and dried at 60° C. The dried organoclay is ground using a hammer mill or similar grinding apparatus to reduce the particle size and then sieved through a 200-mesh screen prior to use. Amounts of reactants used are set forth in Table 1. Screen size was U.S. Standard mesh.

Method A. The organic anion is added to the clay slurry and reacted for approximately 10 minutes followed by addition of the organic cation. The amounts of organic materials added are set forth in the Tables and expressed in milliequivalents of the organic cation and organic anion per 100 g of clay, 100% active clay basis.

Method B. The organic cation is added to the clay slurry in an amount up to and including sufficient cation to satisfy the cation exchange capacity of the clay followed by the addition of the organic anion in the amounts specified in the Tables and permitted to react for 1 to 10 minutes. Additional organic cation was then added to at least satisfy the total cationic exchange capacity.

Method C. A complex comprising the organic cation-organic anion was prepared by admixing appropriate quantities of the organic cation and the sodium salt of the organic anion in solution (water and/or 2-propanol) at a 20 to 90% solids basis. The complex was then added as a solution and reacted with the clay slurry for a period of 10 to 60 minutes.

Results are set forth in Table I and I(a). The abbreviation M.E. stands for milliequivalent ratio.

TABLE I

| Example No. Inventive | Method of Preparation | Alkyl Group of benzyl dimethyl alkyl ammonium Chloride | Organic Cation M.E. Ratio | Organic Anion | Organic Anion M.E. Ratio |
|---|---|---|---|---|---|
| 1 | A | Hydrogenated tallow | 122.5 | disodium phthalate | 22.5 |
| 2 | B | Hydrogenated tallow | 122.5 | disodium phthalate | 22.5 |
| 3 | C | Hydrogenated tallow | 100 | disodium phthalate | 100 |
| 4 | C | Hydrogenated tallow | 120 | disodium phthalate | 120 |
| 5 | C | Hydrogenated tallow | 140 | disodium phthalate | 140 |
| 6 | C | Hydrogenated tallow | 160 | disodium phthalate | 160 |
| 7 | C | Hydrogenated tallow | 122.5 | disodium phthalate | 22.5 |

TABLE I(a)

Solvent Compatibility

| Example No. | Toluene Swelling Volume | Toluene Settling Volume | Methyl isobutyl ketone Swelling Volume | Methyl isobutyl ketone Settling Volume | 60/40 Di-isodecyl Phthalate/Toluene Swelling Volume | 60/40 Di-isodecyl Phthalate/Toluene Settling Volume | n-Butyl Acetate Swelling Volume | n-Butyl Acetate Settling Volume |
|---|---|---|---|---|---|---|---|---|
| 1 | 14 | 22 | 23 | 31 | 18 | 24 | 14 | 17 |
| 2 | 16 | 35 | 22 | 30 | 20 | 31 | 15 | 18 |
| 3 | 14 | 32 | 26 | 53 | 14 | 18 | 12 | 15 |
| 4 | 17 | 96 | 25 | 52 | 19 | 64 | 16 | 18 |
| 5 | 12 | 100 | 18 | 42 | 26 | 92 | 22 | 36 |
| 6 | 11 | 100 | 15 | 27 | 17 | 32 | 14 | 24 |

TABLE I(a)-continued

| | Solvent Compatibility | | | | | | | |
|---|---|---|---|---|---|---|---|---|
| | Solvent | | | | | | | |
| | Toluene | | Methyl isobutyl ketone | | 60/40 Di-isodecyl Phthalate/Toluene | | n-Butyl Acetate | |
| Example No. | Swelling Volume | Settling Volume | Swelling Volume | Settling Volume | Swelling Volume | Settling Volume | Swelling Volume | Settling Volume |
| 7 | 16 | 96 | 24 | 55 | 23 | 72 | 18 | 19 |

EXAMPLES 8–34 and COMPARATIVE EXAMPLES 1 and 2

These examples demonstrate the preparations of organophilic clays of this invention according to Example 1 using various aromatic carboxylic acids as their sodium salt and using benzyl dimethyl alkyl ammonium chloride as the organic cation. The compositions are set forth in Table II with the solvent compatibility results The results indicate that the compositions of this invention are superior rheological additives when compared to conventionally available organophilic clays. Note that the amount of swelling volume and settling volume achieved in various solvents for the conventionally prepared organophilic clay set forth in the comparative examples 1 and 2 demonstrate the inferior dispersibility of these organophilic clays when compared to the inventive compositions.

TABLE II

| Example No. | Alkyl Group of the Benzyl Dimethyl Alkyl Ammonium Chlorides | Organic Cation M.E. Ratio | Organic Anion | Organic Anion M.E. Ratio |
|---|---|---|---|---|
| Comparative 1 | Hydrogenated tallow | 102 | None | None |
| Comparative 2 | Hydrogenated tallow | 110 | None | None |
| Inventive 8 | Hydrogenated tallow | 122.5 | Benzoate | 22.5 |
| 9 | Hydrogenated tallow | 115 | o-Phthalate | 15 |
| 10 | Hydrogenated tallow | 122.5 | o-Phthalate | 22.5 |
| 11 | Hydrogenated tallow | 130 | o-Phthalate | 30 |
| 12 | Hydrogenated tallow | 122.5 | 1,2,3-Benzene tricarboxylate | 22.5 |
| 13 | Hydrogenated tallow | 122.5 | 1,2,4-Benzene tricarboxylate | 22.5 |
| 14 | Hydrogenated tallow | 122.5 | 1,3,5-Benzene tricarboxylate | 22.5 |
| 15 | Hydrogenated tallow | 122.5 | Pyromellitate | 22.5 |
| 16 | Hydrogenated tallow | 115 | Benzophenone tetracarboxylate | 15 |
| 17 | Hydrogenated tallow | 122.5 | Benzophenone tetracarboxylate | 22.5 |
| 18 | Hydrogenated tallow | 130 | Benzophenone tetracarboxylate | 30 |
| 19 | Hydrogenated tallow | 115 | Mellitate | 15 |
| 20 | Hydrogenated tallow | 122.5 | Mellitate | 22.5 |
| 21 | Hydrogenated tallow | 130 | Mellitate | 30 |
| 22 | Hydrogenated tallow | 122.5 | Salicylate | 22.5 |
| 23 | Hydrogenated tallow | 122.5 | p-Toluate | 22.5 |
| 24 | Hydrogenated tallow | 122.5 | 1-Naphthalene carboxylate | 22.5 |
| 25 | Hydrogenated tallow | 122.5 | 1,8-Naphthalene dicarboxylate | 22.5 |
| 26 | Lauryl | 115 | Benzoate | 15 |
| 27 | Lauryl | 122.5 | Benzoate | 22.5 |
| 28 | Lauryl | 130 | Benzoate | 30 |
| 29 | Lauryl | 115 | o-Phthalate | 15 |
| 30 | Lauryl | 122.5 | o-Phthalate | 22.5 |
| 31 | Lauryl | 130 | o-Phthalate | 30 |
| 32 | Octadecyl | 122.5 | Benzoate | 22.5 |
| 33 | Octadecyl | 132.5 | Benzoate | 22.5 |
| 34 | Octadecyl | 142.5 | Benzoate | 22.5 | in Table II(a).

TABLE II(a)

| | Solvent Compatibility | | | | | | | |
|---|---|---|---|---|---|---|---|---|
| | Solvent | | | | | | | |
| | Toluene | | Methyl isobutyl ketone | | 60/40 Di-isodecyl Phthalate/Toluene | | n-Butyl Acetate | |
| Example No. | Swelling Volume | Settling Volume | Swelling Volume | Settling Volume | Swelling Volume | Settling Volume | Swelling Volume | Settling Volume |
| Comparative 1 | 8 | 12 | 19 | 25 | 21 | 34 | 8 | 11 |
| 2 | 10 | 14 | 25 | 35 | 15 | 16 | 19 | 25 |
| Inventive 8 | 22 | 50 | 22 | 43 | 16 | 18 | 24 | 26 |
| 9 | 14 | 22 | 24 | 35 | 16 | 23 | 15 | 18 |
| 10 | 14 | 22 | 23 | 31 | 18 | 24 | 14 | 17 |
| 11 | 18 | 26 | 26 | 45 | 27 | 46 | 23 | 39 |
| 12 | 16 | 58 | 26 | 56 | 20 | 48 | — | — |
| 13 | 20 | 45 | 26 | 56 | 26 | 40 | — | — |
| 14 | 20 | 40 | 26 | 45 | 22 | 34 | 24 | 36 |
| 15 | 19 | 50 | 24 | 48 | 33 | 48 | 26 | 40 |
| 16 | 19 | 36 | 28 | 60 | 23 | 28 | 25 | 41 |
| 17 | 22 | 48 | 30 | 62 | 32 | 55 | 27 | 52 |
| 18 | 17 | 57 | 22 | 46 | 24 | 43 | 20 | 32 |

TABLE II(a)-continued

Solvent Compatibility

| | Solvent | | | | | | | |
|---|---|---|---|---|---|---|---|---|
| | Toluene | | Methyl isobutyl ketone | | 60/40 Di-isodecyl Phthalate/Toluene | | n-Butyl Acetate | |
| Example No. | Swelling Volume | Settling Volume | Swelling Volume | Settling Volume | Swelling Volume | Settling Volume | Swelling Volume | Settling Volume |
| 19 | 11 | 16 | 23 | 33 | 14 | 16 | 20 | 26 |
| 20 | 17 | 96 | 28 | 69 | 27 | 59 | 28 | 50 |
| 21 | 16 | 85 | 25 | 51 | 29 | 94 | 25 | 54 |
| 22 | 22 | 43 | 26 | 60 | 24 | 34 | 22 | 32 |
| 23 | 22 | 58 | 24 | 52 | 24 | 28 | 22 | 30 |
| 24 | 24 | 58 | 26 | 65 | 24 | 24 | 18 | 20 |
| 25 | 12 | 100 | 27 | 56 | 22 | 79 | 18 | 23 |
| 26 | 10 | 19 | 24 | 66 | 8 | 11 | 4 | 6 |
| 27 | 9 | 24 | 22 | 78 | 12 | 14 | 8 | 8 |
| 28 | 14 | 51 | 26 | 56 | 19 | 35 | 9 | 11 |
| 29 | 9 | 15 | 24 | 60 | 10 | 14 | 4 | 7 |
| 30 | 16 | 46 | 26 | 64 | 13 | 14 | 4 | 8 |
| 31 | 15 | 68 | 30 | 54 | 12 | 18 | 8 | 12 |
| 32 | 14 | 64 | 25 | 81 | 28 | 98 | 28 | 40 |
| 33 | 10 | 83 | 18 | 67 | 20 | 77 | 24 | 38 |
| 34 | 14 | 98 | 20 | 72 | 18 | 94 | 23 | 44 |

EXAMPLES 35-51

These examples demonstrate the preparations of organophilic clays of this invention according to Example 1 using various alkyl dicarboxylic acids as their sodium salts and using benzyl dimethyl hydrogenated tallow ammonium chloride as the organic cation. The compositions are set forth in Table III with the solvent compatibility results in Table III(a). The data illustrates the much superior dispersion characteristics of the inventive organophilic clays as compared with organophilic clays prepared in the absence of the organic anion.

TABLE III

| Example No. | Organic Anion | Anion M.E. Ratio | Cation M.E. Ratio |
|---|---|---|---|
| 35 | Oxalate | 15 | 115 |
| 36 | Oxalate | 22.5 | 122.5 |
| 37 | Oxalate | 30 | 130 |
| 38 | Malonate | 22.5 | 122.5 |
| 39 | Succinate | 15 | 115 |
| 40 | Succinate | 22.5 | 122.5 |
| 41 | Succinate | 30 | 130 |
| 42 | Adipate | 22.5 | 122.5 |
| 43 | Pimelate | 22.5 | 122.5 |
| 44 | Suberate | 22.5 | 122.5 |
| 45 | Azelate | 22.5 | 122.5 |
| 46 | Sebacate | 15 | 115 |
| 47 | Sebacate | 22.5 | 122.5 |
| 48 | Sebacate | 30 | 130 |
| 49 | Fumarate | 22.5 | 122.5 |
| 50 | 1,4-cyclohexane dicarboxylate | 22.5 | 122.5 |
| 51 | Maleate | 22.5 | 122.5 |

TABLE III(a)

Solvent Compatibility

| | Solvent | | | | | | | |
|---|---|---|---|---|---|---|---|---|
| | Toluene | | Methyl isobutyl ketone | | 60/40 Di-isodecyl Phthalate/Toluene | | n-Butyl Acetate | |
| Example No. | Swelling Volume | Settling Volume | Swelling Volume | Settling Volume | Swelling Volume | Settling Volume | Swelling Volume | Settling Volume |
| 35 | 17 | 39 | 24 | 48 | 16 | 27 | 14 | 19 |
| 36 | 18 | 45 | 25 | 54 | 25 | 50 | 23 | 35 |
| 37 | 16 | 91 | 23 | 46 | 20 | 81 | 19 | 28 |
| 38 | 21 | 50 | 27 | 53 | 27 | 50 | 23 | 41 |
| 39 | 17 | 42 | 21 | 43 | 17 | 29 | 16 | 21 |
| 40 | 19 | 56 | 27 | 45 | 25 | 55 | 26 | 37 |
| 41 | 15 | 64 | 22 | 38 | 22 | 76 | 20 | 27 |
| 42 | 20 | 40 | 28 | 54 | 33 | 43 | 24 | 39 |
| 43 | 14 | 43 | 20 | 42 | 19 | 32 | 17 | 23 |
| 44 | 19 | 32 | 25 | 41 | 26 | 38 | 32 | 33 |
| 45 | 20 | 37 | 29 | 51 | 37 | 89 | 25 | 38 |
| 46 | 15 | 36 | 24 | 45 | 16 | 27 | 17 | 33 |
| 47 | 20 | 39 | 27 | 52 | 33 | 93 | 24 | 36 |
| 48 | 16 | 100 | 23 | 46 | 19 | 34 | 17 | 25 |
| 49 | 22 | 50 | 25 | 70 | 22 | 30 | 20 | 22 |
| 50 | 20 | 40 | 20 | 45 | 18 | 20 | 20 | 22 |
| 51 | 22 | 62 | 22 | 42 | 22 | 25 | 28 | 20 |

EXAMPLES 52-67

These examples demonstrate the preparation of organophilic clays of this invention according to Example 1 using various aliphatic monocarboxylic acids as their sodium salts and using benzyl dimethyl alkyl ammonium chloride as the organic cation. The compositions are set forth in Table IV and the solvent compatibility results are given in Table IV(a).

The data illustrates the much superior dispersion characteristics of the inventive organophilic clay as compared with organophilic clays prepared in the absence of the organic anion.

sodium salt of the analogous acid and using benzyl dimethyl alkyl ammonium chloride as the organic cation. The compositions are set forth in Table V and the solvent compatibility results are given in Table V(a).

The data illustrates that much superior dispersion characteristics of the inventive organophilic clays are

TABLE IV

| Example No. | Alkyl Group of the Benzyl Dimethyl Alkyl Ammonium Chlorides | Organic Cation M.E. Ratio | Organic Anion | Organic Anion M.E. Ratio |
|---|---|---|---|---|
| 52 | Octadecyl | 122.5 | Sodium Octoate | 22.5 |
| 53 | Octadecyl | 122.5 | Sodium Laurate | 22.5 |
| 54 | Octadecyl | 122.5 | Sodium Stearate | 22.5 |
| 55 | Hydrogenated tallow | 122.5 | Sodium Octoate | 22.5 |
| 56 | Hydrogenated tallow | 122.5 | Sodium Laurate | 22.5 |
| 57 | Hydrogenated tallow | 122.5 | Sodium Stearate | 22.5 |
| 58 | Hydrogenated tallow | 122.5 | Sodium Oleate | 22.5 |
| 59 | Hydrogenated tallow | 122.5 | Sodium Cyclohexane carboxylate | 22.5 |
| 60 | Hydrogenated tallow | 122.5 | Sodium Abietate | 22.5 |
| 61 | Hydrogenated tallow | 122.5 | Sodium Hexanoate | 22.5 |
| 62 | Hydrogenated tallow | 122.5 | Sodium 2-Ethylhexanoate | 22.5 |
| 63 | Lauryl | 115 | Sodium Stearate | 15 |
| 64 | Lauryl | 122.5 | Sodium Stearate | 22.5 |
| 65 | Lauryl | 130.0 | Sodium Stearate | 30 |
| 66 | Hydrogenated tallow | 122.5 | Sodium Cinnanate | 22.5 |
| 67 | Hydrogenated tallow | 122.5 | Sodium Phenylacetate | 22.5 |

TABLE IV(a)

Solvent Compatibility

| Example No. | Toluene | | Methyl isobutyl ketone | | 60/40 Di-isodecyl Phthalate/Toluene | | n-Butyl Acetate | |
|---|---|---|---|---|---|---|---|---|
| | Swelling Volume | Settling Volume | Swelling Volume | Settling Volume | Swelling Volume | Settling Volume | Swelling Volume | Settling Volume |
| 52 | 11 | 90 | 21 | 58 | 20 | 94 | 22 | 34 |
| 53 | 11 | 72 | 22 | 54 | 24 | 23 | 19 | 20 |
| 54 | 15 | 28 | 22 | 53 | 10 | 12 | 8 | 10 |
| 55 | 18 | 74 | 22 | 50 | 26 | 80 | 24 | 34 |
| 56 | 14 | 64 | 22 | 50 | 18 | 42 | 22 | 28 |
| 57 | 18 | 84 | 30 | 54 | 18 | 18 | 20 | 28 |
| 58 | 20 | 84 | 22 | 64 | 22 | 40 | 22 | 24 |
| 59 | 20 | 50 | 22 | 42 | 24 | 50 | 20 | 30 |
| 60 | 18 | 96 | 26 | 80 | 24 | 24 | 22 | 32 |
| 61 | 22 | 48 | 14 | 24 | 28 | 26 | 20 | 24 |
| 62 | 20 | 48 | 22 | 48 | 20 | 18 | 18 | 20 |
| 63 | 12 | 33 | 29 | 58 | 14 | 14 | 6 | 8 |
| 64 | 16 | 56 | 30 | 86 | 16 | 22 | 5 | 8 |
| 65 | 12 | 56 | 25 | 64 | 16 | 40 | 9 | 11 |
| 66 | 20 | 54 | 26 | 53 | 20 | 36 | 20 | 18 |
| 67 | 20 | 48 | 20 | 38 | 20 | 20 | 16 | 16 |

EXAMPLES 68-72

The examples demonstrate the preparation of organophilic clays of this invention according to Example 1 using various organic acids either as the acid or as the sodium salt form, as compared with organophilic clays prepared in the absence of the organic anion.

TABLE V

| Example No. | Quaternary Ammonium Salt | Organic Cation M.E. Ratio | Organic Anion | Form | Organic Anion M.E. Ratio |
|---|---|---|---|---|---|
| 68 | Benzyl Dimethyl Hydrogenated Tallow | 122.5 | Mellitate | Acid | 22.5 |
| 20 | Benzyl Dimethyl Hydrogenated Tallow | 122.5 | Mellitate | Sodium Salt | 22.5 |
| 69 | Benzyl Dimethyl Octadecyl | 122.5 | Octoate | Acid | 22.5 |
| 52 | Benzyl Dimethyl Octadecyl | 122.5 | Octoate | Sodium Salt | 22.5 |
| 70 | Benzyl Dimethyl Octadecyl | 122.5 | Laurate | Acid | 22.5 |
| 53 | Benzyl Dimethyl Octadecyl | 122.5 | Laurate | Sodium Salt | 22.5 |
| 71 | Benzyl Dimethyl Octadecyl | 122.5 | Stearate | Acid | 22.5 |
| 54 | Benzyl Dimethyl Octadecyl | 122.5 | Stearate | Sodium Salt | 22.5 |
| 72a | Benzyl Dimethyl Octadecyl | 122.5 | 12-Hydroxystearate | Acid | 22.5 |
| 72b | Benzyl Dimethyl Octadecyl | 122.5 | 12-Hydroxystearate | Sodium Salt | 22.5 |

TABLE V(a)

| | Solvent Compatibility | | | | | | | |
|---|---|---|---|---|---|---|---|---|
| | Solvent | | | | | | | |
| | Toluene | | Methyl isobutyl ketone | | 60/40 Di-isodecyl Phthalate/Toluene | | n-Butyl Acetate | |
| Example No. | Swelling Volume | Settling Volume | Swelling Volume | Settling Volume | Swelling Volume | Settling Volume | Swelling Volume | Settling Volume |
| 68 | 18 | 29 | 30 | 51 | 19 | 34 | 16 | 20 |
| 20 | 17 | 96 | 28 | 69 | 27 | 59 | 28 | 50 |
| 69 | 13 | 95 | 28 | 76 | 24 | 98 | 23 | 34 |
| 52 | 11 | 90 | 21 | 58 | 20 | 94 | 22 | 34 |
| 70 | 10 | 95 | 26 | 70 | 18 | 38 | 18 | 22 |
| 53 | 11 | 72 | 22 | 54 | 24 | 23 | 19 | 20 |
| 71 | 13 | 32 | 23 | 74 | 11 | 12 | 8 | 9 |
| 54 | 15 | 28 | 22 | 53 | 10 | 12 | 8 | 10 |
| 72a | 10 | 63 | 27 | 71 | 15 | 17 | 14 | 16 |
| 72b | 10 | 74 | 28 | 69 | 17 | 20 | 16 | 16 |

EXAMPLES 73-81

The examples demonstrate the preparation of organophilic clays of this invention according to Example 1 using various hydroxyalkyl carboxylic acids as their sodium salt and using benzyl dimethyl alkyl ammonium chloride as the cation. The compositions are set forth in Table VI and the solvent compatibility results are given in Table VI(a).

The data illustrates the much superior dispersion characteristics of the inventive organophilic clays as compared with organophilic clays prepared in the absence of the organic anion.

EXAMPLES 82-85

These examples demonstrate the preparation of organophilic clays according to this invention according to Example 1 using various amino acids as their sodium derivative and using benzyl dimethyl alkyl ammonium chloride as the organic cation. The compositions are set forth in Table VII and the solvent compatibility results are given in Table VII(a).

The data illustrates that the much superior dispersion characteristics of the inventive organophilic clays as compared with organophilic clays prepared in the absence of the organic anion.

TABLE VI

| Example No. | Alkyl Group of the Benzyl Dimethyl Alkyl Ammonium Chlorides | Organic Cation M.E. Ratio | Organic Anion | Organic Anion M.E. Ratio |
|---|---|---|---|---|
| 73 | Hydrogenated tallow | 115 | Sodium Citrate | 15 |
| 74 | Hydrogenated tallow | 122.5 | Sodium Citrate | 22.5 |
| 75 | Hydrogenated tallow | 130 | Sodium Citrate | 30 |
| 76 | Hydrogenated tallow | 115 | Sodium d-tartrate | 15 |
| 77 | Hydrogenated tallow | 122.5 | Sodium d-tartrate | 22.5 |
| 78 | Hydrogenated tallow | 130 | Sodium d-tartrate | 30 |
| 79 | Hydrogenated tallow | 122.5 | Sodium 12-Hydroxystearate | 22.5 |
| 80 | Hydrogenated tallow | 122.5 | Sodium Malate | 22.5 |
| 81 | Octadecyl | 122.5 | 12-Hydroxystearic Acid | 22.5 |
| 72b | Octadecyl | 122.5 | Sodium 12-Hydroxystearate | 22.5 |

TABLE VI(a)

| | Solvent Compatibility | | | | | | | |
|---|---|---|---|---|---|---|---|---|
| | Solvent | | | | | | | |
| | Toluene | | Methyl isobutyl ketone | | 60/40 Di-isodecyl Phthalate/Toluene | | n-Butyl Acetate | |
| Example No. | Swelling Volume | Settling Volume | Swelling Volume | Settling Volume | Swelling Volume | Settling Volume | Swelling Volume | Settling Volume |
| 73 | 18 | 39 | 22 | 37 | 19 | 29 | 15 | 20 |
| 74 | 19 | 43 | 27 | 63 | 33 | 100 | 24 | 40 |
| 75 | 16 | 93 | 20 | 40 | 23 | 53 | 19 | 27 |
| 76 | 16 | 42 | 24 | 44 | 15 | 26 | 12 | 19 |
| 77 | 18 | 38 | 22 | 38 | 31 | 70 | 22 | 36 |
| 78 | 15 | 100 | 25 | 44 | 22 | 53 | 15 | 18 |
| 79 | 18 | 56 | 28 | 74 | 20 | 18 | 28 | 70 |
| 80 | 18 | 68 | 24 | 60 | 24 | 24 | 20 | 18 |
| 81 | 10 | 63 | 27 | 71 | 15 | 17 | 14 | 16 |
| 72b | 10 | 74 | 28 | 68 | 17 | 20 | 16 | 16 |

TABLE VII

| Example No. | Alkyl Group of the Benzyl Dimethyl Alkyl Ammonium Chlorides | Organic Cation M.E. Ratio | Organic Anion | Organic Anion M.E. Ratio |
|---|---|---|---|---|
| 82 | Hydrogenated tallow | 122.5 | 3-Amino crotonate | 22.5 |

TABLE VII-continued

| Example No. | Alkyl Group of the Benzyl Dimethyl Alkyl Ammonium Chlorides | Organic Cation M.E. Ratio | Organic Anion | Organic Anion M.E. Ratio |
|---|---|---|---|---|
| 83 | Octadecyl | 115 | N—phenylglycinate | 15 |
| 84 | Octadecyl | 122.5 | N—phenylglycinate | 22.5 |
| 85 | Octadecyl | 130 | N—phenylglycinate | 30 |

TABLE VII(a)

Solvent Compatibility

| | Toluene | | Methyl isobutyl ketone | | 60/40 Di-isodecyl Phthalate/Toluene | | n-Butyl Acetate | |
|---|---|---|---|---|---|---|---|---|
| Example No. | Swelling Volume | Settling Volume | Swelling Volume | Settling Volume | Swelling Volume | Settling Volume | Swelling Volume | Settling Volume |
| 82 | 20 | 40 | 22 | 43 | 20 | 22 | 14 | 18 |
| 83 | 22 | 86 | 22 | 76 | 21 | 71 | 24 | 39 |
| 84 | 18 | 52 | 21 | 80 | 24 | 96 | 21 | 32 |
| 85 | 10 | 76 | 19 | 72 | 20 | 92 | 20 | 39 |

EXAMPLES 86-106

The examples demonstrate the preparation of organophilic clays of this invention according to Example 1 using various organic sulfur acids as their sodium salt and using benzyl dimethyl alkyl ammonium chloride as the cation. The compositions are set forth in Table VIII and the solvent compatibility results are given in Table VIII(a).

The data illustrates the much superior dispersion characteristics of the inventive organophilic clays as compared with organophilic clays prepared in the absence of the organic cation.

TABLE VIII

| Example No. | Alkyl Group of the Benzyl Dimethyl Alkyl Ammonium Chlorides | Organic Cation M.E. Ratio | Organic Anion | Organic Anion M.E. Ratio |
|---|---|---|---|---|
| 86 | Hydrogenated tallow | 122.5 | Benzene sulfonate | 22.5 |
| 87 | Hydrogenated tallow | 122.5 | p-Toluene sulfonate | 22.5 |
| 88 | Hydrogenated tallow | 122.5 | Dodecylbenzene sulfonate | 22.5 |
| 89 | Hydrogenated tallow | 122.5 | p-Phenolsulfonate | 22.5 |
| 90 | Hydrogenated tallow | 122.5 | Naphthalene sulfonate | 22.5 |
| 91 | Lauryl | 115 | p-Toluene sulfonate | 15 |
| 92 | Lauryl | 122.5 | p-Toluene sulfonate | 22.5 |
| 93 | Lauryl | 130 | p-Toluene sulfonate | 30 |
| 94 | Hydrogenated tallow | 122.5 | Butane sulfonate | 22.5 |
| 95 | Hydrogenated tallow | 122.5 | Di-isobutyl sulfosuccinate | 22.5 |
| 96 | Hydrogenated tallow | 110 | Dioctyl sulfosuccinate | 10 |
| 97 | Hydrogenated tallow | 120 | Dioctyl sulfosuccinate | 20 |
| 98 | Hydrogenated tallow | 130 | Dioctyl sulfosuccinate | 30 |
| 99 | Hydrogenated tallow | 140 | Dioctyl sulfosuccinate | 40 |
| 100 | Hydrogenated tallow | 150 | Dioctyl sulfosuccinate | 50 |
| 101 | Hydrogenated tallow | 122.5 | Bis (tridecyl) sulfosuccinate | 22.5 |
| 102 | Hydrogenated tallow | 130 | Dioctyl sulfosuccinate Benzoate | 33.4 5.9 |
| 103 | Octadecyl | 122.5 | Alkyl Polyethoxy Sulfosuccinate | 22.5 |
| 104 | Octadecyl | 122.5 | Laurylsulfate | 22.5 |
| 105 | Octadecyl | 132.5 | Laurylsulfate | 22.5 |
| 106 | Octadecyl | 142.5 | Laurylsulfate | 22.5 |

TABLE VIII(a)

Solvent Compatibility

| | Toluene | | Methyl isobutyl ketone | | 60/40 Di-isodecyl Phthalate/Toluene | | n-Butyl Acetate | |
|---|---|---|---|---|---|---|---|---|
| Example No. | Swelling Volume | Settling Volume | Swelling Volume | Settling Volume | Swelling Volume | Settling Volume | Swelling Volume | Settling Volume |
| 86 | 20 | 38 | 24 | 38 | 16 | 18 | 14 | 18 |
| 87 | 18 | 40 | 22 | 42 | 16 | 17 | 15 | 20 |
| 88 | 20 | 38 | 20 | 32 | 16 | 18 | 15 | 20 |
| 89 | 22 | 46 | 26 | 44 | 18 | 22 | 15 | 20 |
| 90 | 20 | 42 | 21 | 36 | 18 | 20 | 18 | 22 |
| 91 | 13 | 26 | 22 | 62 | 11 | 13 | 9 | 9 |
| 92 | 12 | 32 | 22 | 60 | 12 | 12 | 12 | 8 |
| 93 | 18 | 79 | 24 | 60 | 13 | 16 | 10 | 10 |

TABLE VIII(a)-continued

| | Solvent Compatibility | | | | | | | |
|---|---|---|---|---|---|---|---|---|
| | Solvent | | | | | | | |
| | Toluene | | Methyl isobutyl ketone | | 60/40 Di-isodecyl Phthalate/Toluene | | n-Butyl Acetate | |
| Example No. | Swelling Volume | Settling Volume | Swelling Volume | Settling Volume | Swelling Volume | Settling Volume | Swelling Volume | Settling Volume |
| 94 | 22 | 50 | 20 | 34 | 16 | 20 | 18 | 22 |
| 95 | 20 | 30 | 30 | 50 | 21 | 16 | 20 | 18 |
| 96 | 12 | 15 | 22 | 30 | 24 | 38 | 11 | 14 |
| 97 | 13 | 20 | 20 | 30 | 25 | 29 | 14 | 16 |
| 98 | 14 | 20 | 18 | 26 | 22 | 24 | 12 | 14 |
| 99 | 12 | 16 | 17 | 25 | 21 | 34 | 14 | 16 |
| 100 | 13 | 14 | 16 | 25 | 18 | 30 | 14 | 16 |
| 101 | 21 | 24 | 24 | 40 | 22 | 16 | 20 | 18 |
| 102 | 16 | 25 | 19 | 29 | 16 | 20 | 15 | 17 |
| 103 | 10 | 96 | 21 | 89 | 20 | 100 | — | — |
| 104 | 16 | 60 | 22 | 54 | 21 | 44 | 16 | 19 |
| 105 | 10 | 92 | 16 | 24 | 17 | 20 | 8 | 10 |
| 106 | 10 | 98 | 16 | 20 | 16 | 20 | 8 | 8 |

EXAMPLES 107–113

The examples demonstrate the preparation of organophilic clays of this invention according to Example 1 using phenol, a phosphorous acid and miscellaneous anions as their sodium salt and using benzyl dimethyl hydrogenated tallow ammonium chloride as the cation. The compositions are set forth in Table IX and the solvent compatibility results are given in Table IX(a).

The data illustrates the much superior dispersion characteristics of the inventive organophilic clays as compared with organophilic clays prepared in the absence of the organic anion.

TABLE IX

| Example No. | Organic Anion | Organic Anion M.E. Ratio | Organic Cation M.E. Ratio |
|---|---|---|---|
| 107 | Sodium Phenoate | 22.5 | 122.5 |
| 108 | Sodium Epoxystearate | 22.5 | 122.5 |
| 109 | Sodium Tetraphenylborate | 22.5 | 122.5 |
| 110 | Sodium Borate | 22.5 | 122.5 |
| 111 | Sodium Ferrocyanide | 22.5 | 122.5 |
| 112 | Sodium Ferrocyanide | 22.5 | 122.5 |
| 113 | Sodium dioctadecyl phosphite | 22.5 | 122.5 |

1 using various anions as their sodium salt and using dibenzyl dihydrogenated tallow ammonium chloride as the cation. The compositions are set forth in Table X and the solvent compatibility results are given in Table X(a).

The data illustrates that the dispersion characteristics of the inventive organophilic clays prepared from various organic anions using dibenzyl dihydrogenated tallow ammonium chloride fluctuate in the solvent systems tested. It should be noted, however, that when these materials were used to prepare a thixotropic polyester laminating resin that improved results were obtained over the comparative materials.

TABLE X

| Example No. | Organic Anion | Organic Anion M.E. Ratio | Organic Cation M.E. Ratio |
|---|---|---|---|
| 114 | o-phthalate | 15 | 115 |
| 115 | o-phthalate | 30 | 130 |
| 116 | 1,2,3-benzenetricarboxylate | 15 | 115 |
| 117 | 1,2,3-benzenetricarboxylate | 30 | 130 |
| 118 | 1,2,4-benzenetricarboxylate | 15 | 115 |
| 119 | 1,2,4-benzenetricarboxylate | 30 | 130 |
| 120 | 1,2,5-benzenetricarboxylate | 15 | 115 |
| 121 | 1,2,5-benzenetricarboxylate | 30 | 130 |
| 122 | Pyromellitate | 15 | 115 |
| 123 | Pyromellitate | 30 | 130 |
| 124 | Mellitate | 15 | 115 |
| 125 | Mellitate | 30 | 130 |
| 126 | dioctylsulfosuccinate | 15 | 115 |
| comparative example 3 | None | None | 114.7 |

TABLE IX(a)

| | Solvent Compatibility | | | | | | | |
|---|---|---|---|---|---|---|---|---|
| | Solvent | | | | | | | |
| | Toluene | | Methyl isobutyl ketone | | 60/40 Di-isodecyl Phthalate/Toluene | | n-Butyl Acetate | |
| Example No. | Swelling Volume | Settling Volume | Swelling Volume | Settling Volume | Swelling Volume | Settling Volume | Swelling Volume | Settling Volume |
| 107 | 15 | 69 | 25 | 78 | 28 | 83 | 22 | 30 |
| 108 | 24 | 100 | 24 | 65 | 20 | 20 | 22 | 24 |
| 109 | 10 | 27 | 24 | 43 | 18 | 20 | 17 | 26 |
| 110 | 20 | 81 | 23 | 52 | 24 | 28 | 20 | 22 |
| 111 | 16 | 26 | 30 | 74 | 12 | 12 | 13 | 14 |
| 112 | 10 | 14 | 31 | 86 | 11 | 11 | 10 | 12 |
| 113 | 16 | 100 | 25 | 50 | 20 | 12 | 18 | 18 |

EXAMPLES 114–126 and COMPARATIVE EXAMPLE 3

These examples demonstrate the preparation of organophilic clays of this invention according to Example

TABLE X(a)

| Example No. | Methyl isobutyl ketone | | 60/40 Di-isodecyl Phthalate/Toluene | | Hexane | | n-Butyl Acetate | |
|---|---|---|---|---|---|---|---|---|
| | Swelling Volume | Settling Volume | Swelling Volume | Settling Volume | Swelling Volume | Settling Volume | Swelling Volume | Settling Volume |

| Example No. | Swelling Volume | Settling Volume | Swelling Volume | Settling Volume | Swelling Volume | Settling Volume | Swelling Volume | Settling Volume |
|---|---|---|---|---|---|---|---|---|
| 114 | 12 | 52 | 10 | 12 | 10 | 12 | 20 | 33 | 12 | 15 |
| 115 | 12 | 11 | 6 | 8 | 8 | 12 | 26 | 44 | 9 | 14 |
| 116 | 11 | 100 | 9 | 10 | 7 | 8 | 27 | 46 | 10 | 11 |
| 117 | 11 | 100 | 6 | 9 | 6 | 10 | 24 | 71 | 10 | 13 |
| 118 | 13 | 6 | 10 | 13 | 9 | 15 | 20 | 31 | 12 | 17 |
| 119 | 14 | 100 | 9 | 11 | 8 | 12 | 34 | 48 | 12 | 17 |
| 120 | 12 | 46 | 10 | 13 | 10 | 12 | 16 | 23 | 11 | 13 |
| 121 | 15 | 100 | 8 | 10 | 18 | 12 | 27 | 33 | 11 | 16 |
| 122 | 12 | 8 | 10 | 13 | 9 | 14 | 17 | 25 | 12 | 17 |
| 123 | 12 | 100 | 9 | 11 | 8 | 13 | 36 | 50 | 12 | 18 |
| 124 | 13 | 3 | 9 | 12 | 8 | 10 | 25 | 37 | 11 | 12 |
| 125 | 13 | 2 | 6 | 8 | 7 | 10 | 26 | 82 | 10 | 14 |
| 126 | 15 | 21 | 10 | 11 | 8 | 10 | 20 | 30 | 10 | 12 |
| comparative example 3 | 14 | 93 | 11 | 14 | 11 | 12 | 24 | 46 | 10 | 14 |

EXAMPLES 127 to 132 and COMPARATIVE materials coupled with outstanding improvement in other solvent systems.

TABLE XI

| Example No. | Quaternary Ammonium Chloride | Organic Cation M.E. Ratio | Organic Anion | Organic Anion M.E. Ratio |
|---|---|---|---|---|
| comparative example 4 | Dimethyl Di (Hydrogenated tallow) | 95 | None | None |
| 127 | Dimethyl Di (Hydrogenated tallow) | 122.5 | o-Phthalate | 22.5 |
| 128 | Dimethyl Di (Hydrogenated tallow) | 122.5 | Mellitate | 22.5 |
| 129 | Dimethyl Di (Hydrogenated tallow) | 122.5 | Citrate | 22.5 |
| comparative example 5 | Benzyl Methyl Di (Hydrogenated tallow) | 112 | None | None |
| 130 | Benzyl Methyl Di (Hydrogenated tallow) | 122.5 | o-Phthalate | 22.5 |
| comparative example 6 | Trimethyl Hydrogenated tallow | 111 | None | None |
| 131 | Trimethyl Hydrogenated tallow | 122.5 | o-Phthalate | 22.5 |
| comparative example 7 | Methyl Tri (Hydrogenated tallow) | 111 | None | None |
| 132 | Methyl Tri (Hydrogenated tallow) | 122.5 | o-Phthalate | 22.5 |

TABLE XI(a)

| Example No. | Toluene | | Methyl isobutyl ketone | | 60/40 Di-isodecyl Phthalate/Toluene | | Hexane | |
|---|---|---|---|---|---|---|---|---|
| | Swelling Volume | Settling Volume | Swelling Volume | Settling Volume | Swelling Volume | Settling Volume | Swelling Volume | Settling Volume |
| comparative example 4 | 12 | 20 | 14 | 17 | 16 | 24 | 5 | 6 |
| 127 | 13 | 100 | 12 | 16 | 13 | 22 | 25 | 36 |
| 128 | 11 | 5 | 8 | 10 | 8 | 13 | 14 | 17 |
| 129 | 11 | 77 | 9 | 13 | 12 | 16 | 14 | 19 |
| comparative example 5 | 13 | 27 | 12 | 14 | 14 | 20 | 11 | 14 |
| 130 | 10 | 100 | 11 | 14 | 16 | 23 | 21 | 32 |
| comparative example 6 | 14 | 21 | 18 | 22 | 21 | 34 | 2 | 2 |
| 131 | 16 | 34 | 17 | 24 | 20 | 45 | 2 | 3 |
| comparative example 7 | 12 | 60 | 7 | 10 | 12 | 8 | 19 | 40 |
| 132 | 8 | 100 | 5 | 8 | 10 | 17 | 35 | 100 |

EXAMPLES 4 to 7

The examples demonstrate the preparation of organophilic clays of this invention according to Example 1 using various organic acids as their sodium salt and using various organic ammonium salts as the cation. The compositions are set forth in Table XI and the solvent compatibility results are given in Table XI(a).

The results indicate that inventive organophilic clay prepared from different quaternary ammonium compounds result in the formation of materials having dispersion properties at least as good as the comparative materials coupled with outstanding improvement in other solvent systems.

EXAMPLES 133 to 134 and COMPARATIVE EXAMPLES 8-10

The examples demonstrate the preparation of organophilic clays of this invention according to Example 1 using both Wyoming bentonite or hectorite along with various organic cations and disodium ortho-phthalate as the organic anion. Results are given in Tables XII and XII(a).

The results indicate that the inventive organophilic clays exhibit dispersion properties at least as good as the comparative materials coupled with outstanding improvements in other solvent systems.

TABLE XII

| Example No. | Quaternary Ammonium Chloride | Organic Cation M.E. Ratio | Organic Anion | Organic Anion M.E. Ratio | Type of Clay |
|---|---|---|---|---|---|
| comparative example 4 | Dimethyl Di (Hydrogenated tallow) | 95 | None | None | Wyoming Bentonite |
| comparative example 8 | Dimethyl Di (Hydrogenated tallow) | 95 | None | None | Hectorite |
| 127 | Dimethyl Di (Hydrogenated tallow) | 122.5 | o-Phthalate | 22.5 | Wyoming Bentonite |
| 133 | Dimethyl Di (Hydrogenated tallow) | 122.5 | o-Phthalate | 22.5 | Hectorite |
| comparative example 9 | Benzyl Dimethyl Hydrogenated tallow | 102 | None | None | Hectorite |
| comparative example 10 | Benzyl Dimethyl Hydrogenated tallow | 95 | None | None | Wyoming Bentonite |
| 134 | Benzyl Dimethyl Hydrogenated tallow | 122.5 | o-Phthalate | 22.5 | Hectorite |
| 130 | Benzyl Dimethyl Hydrogenated tallow | 122.5 | o-Phthalate | 22.5 | Wyoming Bentonite |

TABLE XII(a)

| | Toluene | | Methyl isobutyl ketone | | Hexane | |
|---|---|---|---|---|---|---|
| Example No. | Swelling Volume | Settling Volume | Swelling Volume | Settling Volume | Swelling Volume | Settling Volume |
| comparative example 4 | 12 | 20 | 14 | 17 | 5 | 6 |
| comparative example 8 | 9 | 11 | 11 | 12 | 5 | 4 |
| 127 | 13 | 100 | 12 | 16 | 25 | 36 |
| 133 | 6 | 100 | 10 | 14 | 20 | 25 |
| comparative example 9 | 4 | 6 | 14 | 16 | 2 | 3 |
| comparative example 10 | 8 | 12 | 19 | 25 | 4 | 5 |
| 134 | 11 | 20 | 16 | 21 | 3 | 4 |
| 130 | 14 | 22 | 23 | 31 | 4 | 4 |

EXAMPLES 135 to 168 and COMPARATIVE EXAMPLES 11 to 16

These examples demonstrate the use of the aforementioned organophilic clays in thixotropic polyester compositions.

Unsaturated polyester compositions comprising polyesters based on unsaturated acids or acid anhydrides and diols in admixture with unsaturated aromatic monomers such as styrene have been described heretofore for the production of cross-linked polymers initiated by peroxides. In the preparation of glass fiber-reinforced laminates of these cross-linked polymers, thixotropic gelling agents are employed which decrease the viscosity of the uncross-linked polyester at high shear such as is developed in mixing and spraying but which increases their viscosity at low or no shear to prevent drainage of the composition along the vertical surfaces to which they are applied.

In the past, asbestos and fine particle size silica have acted as efficient gelling agents for such polyester compositions. However asbestos presents health hazards whereas fumed silica often reduces the clarity and shelflife of compositions in which it is contained.

In an effort to depart from the use of fumed silica and asbestos as gelling agents, certain organophilic clays, which have heretofore been effective gellants for liquid hydrocarbon systems, have been employed as gellants for unsaturated polyester compositions. Such organophilic clays can be described as the reaction product of a natural or synthetic clay and a higher alkyl-containing quaternary ammonium compound. For purposes of brevity, these organophilic clays are often named as compounds rather than reaction products, e.g. dimethyl dioctadecyl ammonium bentonite or benzyl methyl ditallow ammonium hectorite. See U.S. Pat. Nos. 3,974,125 and 4,216,135. Although the organophilic clay gellants of these patents provide thixotropic properties to the final polyester composition, they must be employed in the form of handleable pregels in monomeric styrene.

In contrast the organophilic clays of this invention may be used without the need for a styrene pregel. In particular, polyester compositions may be prepared by mixing the organophilic clay with the final liquid polyester mixture prepared from a liquid unsaturated polyester and unsaturated aromatic monomer. The final polyester compositions can then be cross-linked to produce coatings or glass fiber-reinforced laminates by methods well known in the art.

In a typical procedure the liquid unsaturated polyester resin is mixed in conventional apparatus with an unsaturated aromatic monomer to prepare a solution having a solids content between about 40 and 95% by weight polyester. The organophilic clays of the invention can then be added to the liquid laminating resin and mixed in under low shear conditions to form a homogenous mixture. This mixture is then subjected to high shear to disperse the organophilic clay to achieve full viscosity levels.

The unsaturated aromatic monomers of this invention are aromatic compounds to which is bonded one or more ethylenically unsaturated radical such as a vinyl radical, substituted vinyl radical or an allylic radical. Suitable monomers include styrene, α-methyl styrene, divinyl benzene and allyl benzene. Styrene is preferred due to its effectiveness, wide use and availability. Such monomers are used in cross-linking the polyesters and also act as diluents to reduce viscosity.

The unsaturated polyesters useful in preparing the thixotropic compositions of this invention are polyesters of a dicarboxylic acid and a diol having a major amount of olefinic unsaturation, preferably 10 to 75 olefin groups per 100 ester groups. The olefinic unsaturation is preferably derived from the carboxylic acid although the diol may be unsaturated. Typical diols are ethylene glycol and propylene glycol. Typical unsaturated acids include maleic acid, fumaric acid. Anhydrides of these acids are also commonly used. Such polyesters are made by conventional techniques of esterification as well known in the art. Generally, polyesters having molecular weights of from about 400 to 10,000 and acid numbers in the range of from 35 to 45 mg KOH per gram of resin are useful for preparing thixotropic compositions of this invention.

The amounts of organophilic clay gellant used in polyester laminating resins can range from 0.25% to 10%, preferably 0.5 to 4%. Amounts larger than 10% may be employed even though such levels are not economical and may form an unhandleable resin system.

In order to more completely describe the present invention, the following examples are given. All percentages given are based upon weight unless otherwise indicated.

The organophilic clays of this invention were predispersed in a 56% solids unsaturated polyester laminating resin prepared from a unsaturated polyester formulation comprising 56% of an unsaturated polyester resin and 44% of styrene in an amount to provide a 1% concentration of the organophilic clay in the final mixture. The predispersion was accomplished using a low speed mixer for 10 minutes. The mixture was then subjected to high shear by use of a laboratory mixing apparatus (Sonolator) to form a thickened polyester composition.

For comparison purposes the organophilic clay was replaced with fine particle size fumed silica at 1% by weight levels.

Viscosity data for the resin systems were determined using a Brookfield RVT viscometer using a No. 2 spindle. The thixotropic index is a ratio of the viscosities taken at 6 and 60 rpm. Results are set forth in Tables XIII and XIV.

Tables XIII and XIV show that the organophilic clay gellants of this invention impart higher viscosities to the polyester compositions, a higher Thixotropic Index and a better rheology than the comparison examples.

TABLE XIII

| Example No. | Quaternary Ammonium Chloride | Organic Cation M.E. Ratio | Organic Anion, Sodium Salt of | Organic Anion M.E. Ratio | Type of Clay |
|---|---|---|---|---|---|
| comparative 11 | Dimethyl Di (Hydrogenated tallow) | 95 | None | None | Hectorite |
| 135 | Dimethyl Di (Hydrogenated tallow) | 122.5 | phthalate | 22.5 | Hectorite |
| 136 | Dimethyl Di (Hydrogenated tallow) | 122.5 | phthalate | 22.5 | Wyoming Bentonite |
| comparative 12 | Trimethyl Hydrogenated tallow | 111 | None | None | Wyoming Bentonite |
| 137 | Trimethyl Hydrogenated tallow | 122.5 | phthalate | 22.5 | Wyoming Bentonite |
| comparative 13 | Dibenzyl Di (Hydrogenated tallow) | 110 | None | None | Wyoming Bentonite |
| 138 | Dibenzyl Di (Hydrogenated tallow) | 115 | 1,2,3-benzene tricarboxylate | 15 | Wyoming Bentonite |
| 139 | Dibenzyl Di (Hydrogenated tallow) | 130 | 1,2,3-benzene tricarboxylate | 30 | Wyoming Bentonite |
| 140 | Dibenzyl Di (Hydrogenated tallow) | 115 | 1,2,4-benzene tricarboxylate | 15 | Wyoming Bentonite |
| 141 | Dibenzyl Di (Hydrogenated tallow) | 130 | 1,2,4-benzene tricarboxylate | 30 | Wyoming Bentonite |
| 142 | Dibenzyl Di (Hydrogenated tallow) | 115 | 1,3,5-benzene tricarboxylate | 15 | Wyoming Bentonite |
| 143 | Dibenzyl Di (Hydrogenated tallow) | 130 | 1,3,5-benzene tricarboxylate | 30 | Wyoming Bentonite |
| 144 | Dibenzyl Di (Hydrogenated tallow) | 115 | dioctyl sulfosuccinate | 15 | Wyoming Bentonite |
| comparative 14 | Methyl Tri (Hydrogenated tallow) | 114 | None | None | Wyoming Bentonite |
| 145 | Methyl Tri (Hydrogenated tallow) | 122.5 | phthalate | 22.5 | Wyoming Bentonite |
| 146 (See Example 1 Method C) | Benzyl Dimethyl Hydrogenated tallow | 100 | phthalate | 100 | Wyoming Bentonite |

TABLE XIII(a)

| | EXPERIMENTAL RHEO. | | | | FUMED SILICA | | | |
|---|---|---|---|---|---|---|---|---|
| Example No. | 6 RPM Viscosity | 60 RPM Viscosity | Thixotropic Index | Sag (mils) | 6 RPM Viscosity | 60 RPM Viscosity | Thixotropic Index | Sag (mils) |
| comparative example 11 | 250 | 250 | 1.0 | <4 | 1500 | 518 | 2.9 | 6 |
| 135 | 800 | 400 | 1.8 | 6 | 1500 | 518 | 2.9 | 6 |
| 136 | 800 | 480 | 1.7 | 7 | 1500 | 518 | 2.9 | 6 |
| comparative example 12 | 550 | 325 | 1.7 | 5 | 1500 | 518 | 2.9 | 6 |
| 137 | 800 | 440 | 1.8 | 6 | 1500 | 518 | 2.9 | 6 |
| comparative example 13 | 400 | 275 | 1.5 | <4 | 1200 | 593 | 2.1 | 6 |
| 138 | 1000 | 558 | 1.8 | 12 | 1640 | 670 | 2.4 | 12 |
| 139 | 600 | 452 | 1.3 | 7 | 1640 | 670 | 2.4 | 12 |
| 140 | 1000 | 560 | 1.8 | 11 | 1640 | 670 | 2.4 | 12 |
| 141 | 900 | 500 | 1.8 | 6 | 1640 | 670 | 2.4 | 12 |
| 142 | 2000 | 650 | 3.1 | 10 | 1640 | 670 | 2.4 | 12 |
| 143 | 800 | 495 | 1.6 | 6 | 1640 | 670 | 2.4 | 12 |
| 144 | 800 | 500 | 1.6 | 6 | 1640 | 670 | 2.4 | 12 |
| comparative 14 | 600 | 400 | 1.5 | 4 | 1500 | 518 | 2.9 | 6 |
| 145 | 900 | 460 | 1.9 | 7 | 1500 | 518 | 2.9 | 6 |
| 146 | 80 | 484 | 1.7 | 8 | 1640 | 670 | 2.4 | 12 |

TABLE XIV

| Example No. | Organic Anion | Organic Anion M.E. Ratio | Organic Cation M.E. Ratio | Type of Clay |
|---|---|---|---|---|
| comparative example 15 | None | None | 102 | Wyoming Bentonite |
| comparative example 16 | None | None | 102 | Hectorite |
| 147 | Sodium Oxalate | 22.5 | 122.5 | Wyoming Bentonite |
| 148 | Sodium Malonate | 22.5 | 122.5 | Wyoming Bentonite |
| 149 | Sodium Succinate | 22.5 | 122.5 | Wyoming Bentonite |
| 150 | Sodium Adipate | 22.5 | 122.5 | Wyoming Bentonite |

TABLE XIV-continued

| Example No. | Organic Anion | Organic Anion M.E. Ratio | Organic Cation M.E. Ratio | Type of Clay |
|---|---|---|---|---|
| 151 | Sodium Suberate | 22.5 | 122.5 | Wyoming Bentonite |
| 152 | Sodium Azelate | 22.5 | 122.5 | Wyoming Bentonite |
| 153 | Sodium Sebaccate | 22.5 | 122.5 | Wyoming Bentonite |
| 154 | Sodium Citrate | 22.5 | 122.5 | Wyoming Bentonite |
| 155 | Sodium d-tartrate | 22.5 | 122.5 | Wyoming Bentonite |
| 156 | Sodium Phthalate | 22.5 | 122.5 | Wyoming Bentonite |
| 157 | Sodium Phthalate | 30 | 130 | Wyoming Bentonite |
| 158 | Sodium Phthalate | 22.5 | 122.5 | Hectorite |
| 159 | Sodium 1,3,5-Benzene Tricarboxylate | 22.5 | 122.5 | Wyoming Bentonite |
| 160 | Sodium 1,3,5-Benzene Tricarboxylate | 22.5 | 122.5 | Wyoming Bentonite |
| 161 | Sodium 1,2,4-Benzene Tricarboxylate | 22.5 | 122.5 | Wyoming Bentonite |
| 162 | Sodium Pyromelliate | 22.5 | 122.5 | Wyoming Bentonite |
| 163 | Sodium Benzophenone Tetracarboxylate | 15 | 115 | Wyoming Bentonite |
| 164 | Sodium Benzophenone Tetracarboxylate | 22.5 | 122.5 | Wyoming Bentonite |
| 165 | Sodium Mellitate | 15 | 115 | Wyoming Bentonite |
| 166 | Sodium Mellitate | 22.5 | 122.5 | Wyoming Bentonite |
| 167 | Sodium Mellitate | 30 | 130 | Wyoming Bentonite |
| 168 | Mellitic Acid | 22.5 | 122.5 | Wyoming Bentonite |

TABLE XIV(a)

| Example No. | EXPERIMENTAL ORGANOPHILIC CLAY | | | | FUMED SILICA | | | |
|---|---|---|---|---|---|---|---|---|
| | 6 RPM Viscosity | 60 RPM Viscosity | Thixotropic Index | Sag (mils) | 6 RPM Viscosity | 60 RPM Viscosity | Thixotropic Index | Sag (mils) |
| comparative 15 | 350 | 265 | 1.3 | <4 | 1500 | 518 | 2.9 | 6 |
| Comparative 16 | 250 | 230 | 1.1 | <4 | 1500 | 518 | 2.9 | 6 |
| 147 | 1440 | 572 | 2.5 | 9 | 1500 | 518 | 2.9 | 6 |
| 148 | 1120 | 628 | 1.8 | 12 | 1640 | 670 | 2.9 | 12 |
| 149 | 1120 | 568 | 2.0 | 9 | 1500 | 518 | 2.9 | 6 |
| 150 | 1000 | 528 | 1.9 | 8 | 1500 | 518 | 2.9 | 6 |
| 151 | 1600 | 720 | 2.2 | 12 | 1640 | 670 | 2.4 | 12 |
| 152 | 1200 | 604 | 2.0 | 12 | 1640 | 670 | 2.4 | 12 |
| 153 | 980 | 548 | 1.8 | 8 | 1500 | 518 | 2.9 | 6 |
| 154 | 1860 | 720 | 2.6 | 5 | 1640 | 670 | 2.4 | 12 |
| 155 | 1700 | 750 | 2.3 | <4 | 1640 | 670 | 2.4 | 12 |
| 156 | 1400 | 600 | 2.3 | 7 | 1500 | 518 | 2.9 | 6 |
| 157 | 1000 | 460 | 2.2 | 7 | 1250 | 593 | 2.1 | 6 |
| 158 | 400 | 300 | 1.3 | 6 | 1500 | 518 | 2.9 | 6 |
| 159 | 1600 | 600 | 2.7 | 7 | 1200 | 600 | 2.0 | 5 |
| 160 | 1800 | 640 | 2.8 | 7 | 1200 | 600 | 2.0 | 5 |
| 161 | 1400 | 560 | 2.5 | 6 | 1200 | 600 | 2.0 | 5 |
| 162 | 1600 | 600 | 2.7 | 7 | 1200 | 600 | 2.0 | 5 |
| 163 | 1400 | 600 | 2.3 | 7 | 1200 | 600 | 2.0 | 5 |
| 164 | 1400 | 520 | 2.7 | 7 | 1200 | 600 | 2.0 | 5 |
| 165 | 800 | 420 | 1.9 | 6 | 1200 | 600 | 2.0 | 5 |
| 166 | 1400 | 560 | 2.5 | 7 | 1200 | 600 | 2.0 | 5 |
| 167 | 1000 | 520 | 1.9 | 7 | 1200 | 600 | 2.0 | 5 |
| 168 | 1600 | 640 | 2.5 | 10 | 1200 | 600 | 2.0 | 5 |

EXAMPLES 169 to 177 and COMPARATIVE EXAMPLES 17 to 21

The examples demonstrate the use of the aforementioned organophilic clays in thixotropic coating compositions.

Coating compositions comprising a film forming organic and/or inorganic binder, solvents, and optionally pigments have been described heretofore for use as decorative and/or protective materials for e.g., metal, wood, plastics, and paper. In practice, these compositions are applied to the substrate with equipment such as a brush, a roller, air or airless atomization, or dipping. In these compositions, thixotropic gelling agents may be employed which decrease the viscosity of the coating composition at high shear such as would be employed during the application of the coating but which increase the viscosity under low or no shear conditions.

In the past, asbestos, fumed silica, various organic materials, and organophilic clays have been employed as efficient gelling agents for such coating compositions. However, these materials have suffered from various disadvantages, such as creation of health hazards, high cost-performance levels and preparation of inadequate coating compositions lacking in gloss and surface smoothness.

The organophilic clays of this invention have been employed as effective gellants for coating compositions without the difficulties associated with the prior art materials. The organophilic clays may be dispersed in the coating compositions under low or optionally high shear conditions.

In a typical procedure, the organophilic clay gellant is added to a coating composition comprising a film forming organic binder, organic solvent, and optionally pigments under agitation at 5000 lineal feet per minute. The stirring rate is increased to 15,000 lineal feet per minute for 15 minutes to insure complete dispersion of the organophilic clay.

The film forming organic binders of this invention are prepared by conventional procedures such as polymerition of acrylate and methacrylate esters; from saturated polyester resins; and by reaction of drying oils such as linoleic acid with polymers containing hydroxyl functionality. Generally, organic binders having gram molecular weights of 200 to several hundred thousand are useful.

Organic solvents for such coatings may be broadly classified into five categories which include aliphatic, aromatic, moderately polar, polar and chlorinated solvent. Aliphatic solvents include normal and branched chain aliphatic hydrocarbons having from about 5 to 12 carbon atoms and cycloaliphatic compounds. Aromatic solvents include such materials as benzene, toluene, xylene and ethyl benzene. Moderately polar solvents include ketonic and ester solvents such as acetone, methyl ethyl ketone, methyl butyl ketone, methyl isobutyl ketone, cyclohexanone, ethyl acetate, butyl acetate, ethoxyethyl acetate, and the like. Polar solvents include such materials as low molecular weight alcohols such as methanol, ethanol, propanol, 2-propanol, butanol, 2-butanol, and ethoxyethanol. Chlorinated hydrocarbon solvents include such materials as methylene chloride, chloroform, carbon tetrachloride, chloroethane, and 1,1,1-trichloroethane.

The amounts of organophilic clay gellant used in the coating compositions can range from 0.25% to 10%, and preferably 0.5% to 5% by weight. Amounts larger than 10% can be used but are difficult to handle because of high viscosities. The organic binder may be conveniently employed in amounts of 10% to 80% of the liquid portion of the coating composition. The organic solvent is employed in sufficient amounts to reduce the viscosity of the coating composition to usable levels depending on the method of application, but in any case to yield up to 100% of the total composition. Supplemental additives including pigments may be employed in quantities ranging from 0.5 to 50% of the total coating composition.

In order to more completely describe the present invention, the following examples are given. All percentages given are based upon weight unless otherwise indicated. The ingredients and amounts thereof used to prepare each coating composition are summarized in Tables XV (Aliphatic Solvent System), Table XVI (Moderately Polar Solvent System) and Table XVII (Alcohol Based System).

The results in the tables show that the inventive compositions when post-added to a coating system at moderately low shear imparts superior viscosity and sag to the system and is dispersed to almost the same level as conventionally employed materials when incorporated into the system at a significantly higher shear condition. Also, the comparative materials when incorporated into the system at lower shear condition are decidedly inferior in dispersibility, viscosity build and sag resistant properties compared to the inventive material incorporated into the system at the same shear.

The organophilic clays of this invention having the composition as per the Tables were post-added under low shear conditions into the coating composition without a polar solvent activator. For comparison, various conventional organoclays were also post-added to the coating composition at the same shear condition as the test organophilic clay; however, in this case a mixture of 95% methanol and 5% water was used as a polar solvent activator for the organoclay.

Specifically, 600 grams of a previously prepared coating composition, not containing a rheological additive, was weighed into a derimmed circular quart can which measures 4 inches in diameter and 4⅝ inches in height. The system is agitated using a 1 HP Premier dispersator equipped with a 1¾ inch diameter saw tooth Cowles blade. The blade was positioned in the system at the center of the quart can at a height such that the bottom of the blade is ½ inch above the bottom surface of the can. The shaft speed is held constant at 3000 rpm. 5.1 grams of the organophilic clays of this invention are slowly sifted into the swirling system. In the case of the comparative materials 1.7 grams (2.1 cc) of a mixture of 95% methanol and 5% water is also added to the system exactly one minute after the addition of the organoclay is completed. This polar solvent activator is injected into the system using a 5 cc glass syringe.

The system plus organoclay plus activator, in the case of the comparative organophilic clay, is allowed to mix at a shaft speed of 3,000 rpm for a total of 5 minutes. At this time, without stopping the dispersator, a small aliquot of solution is withdrawn from the quart can using a tapered 5 inch stainless steel spatula. This aliquot is used to measure the fineness of dispersion of the solution. This measurement is made using a Hegman fineness of grind gauge calib rated in a scale that ranges from 0 to 8 where 0 is equal to a film thickness of 4 mils and 8 is equal to a film thickness of zero mils. The grind gauge is a stainless steel block into which a channel of varying depth has been cut out. The solution to be tested is placed into the channel at the deepest end (zero Hegman) and cast down the full length of the channel. The fineness of grind of the system is determined at the point along the channel depth at which the pigment particles are first visible above the surface of the solution film. This measurement is taken after 5, 7, 9, 11, 13 and 15 minutes mixing time. The systems are then transferred to a tin can and allowed to equilibrate overnight at 20° C. before being tested for viscosity and sag.

The ease of dispersion test is made as discussed bove using a Brookfield RVT model viscometer equipped with a #4 spindle at a spindle speed of 10 rpm. The sag measurements are made with a Leneta anti-sag blade. The sag drawdowns are cast onto Leneta 7B charts with the aid of a mechanical drive film applicator equipped with a perforated vacuum plate. The completed drawdowns are placed in a vertical position with the paint stripes horizontal, the thinnest stripe at the top. The sag is read, after the film has dried, as the thickest stripe which does not sag sufficiently to cross into the next stripe below it. Sag units are in mils (0.001 inch).

In Table XV and XVI, the greater viscosity build and at least equal dispersibility of the organophilic clays of this invention demonstrates the better dispersibility of these clays versus conventionally prepared organophilic clays in aliphatic and moderately polar solvent based coatings compositions.

In Table XVII the greater viscosity build and sag resistance of the organic anion containing organophilic clay demonstrates the superior performance of the organophilic clays of this invention versus a conventionally prepared organophilic clay in a highly polar, alcohol based formulation.

TABLE XV

ALIPHATIC SOLVENT SYSTEM

| INGREDIENTS | GENERIC NAME | MANUFACTURER | BLANK (NO THICKENER) POUNDS | CONTROL NORMAL PROCESSING (HIGH SHEAR) POUNDS | EXPERIMENTAL LOW SHEAR PROCESSING (POST ADDITION) POUNDS |
|---|---|---|---|---|---|
| MILLBASE | | | | | |
| Aroplaz 1266M70 | Long Oil Soya Alkyd Resin Solution (70% N.V.) | Spencer Kellogg Div. of Textron, Inc. | 66.1 | 66.1 | 66.1 |
| Mineral Spirits 663 | Aliphatic Hydrocarbon | Union Oil Company of California | 66.7 | 66.7 | 66.7 |
| Rheological Additive | Dimethyl di-hydrogenated tallow ammonium bentonite | NL Industries, Inc. | — | 10 | — |
| Methanol/Water, 95/5 | — | — | — | 3.3 | — |
| TITANOX 2020 | Titanium Dioxide Rutile | NL Industries, Inc. | 240.1 | 240.1 | 240.1 |
| Atomite | Calcium Carbonate Natural Ground | Thompson, Weinmann & Co. | 191.3 | 191.3 | 191.3 |
| GRIND AT HIGH SPEED - 5400 RPM FOR 15 MINUTES ||||||
| LET DOWN - ADD IN ORDER LISTED WITH MIXING AT 2,000 RPM ||||||
| Aroplaz 1266 M70 | Long Oil Soya Alkyd Resin Solution (70% N.V.) | Spencer Kellogg Div. of Textron, Inc. | 241.4 | 241.4 | 241.4 |
| Aroflat 3113P30 | Tixotropic Alkyd | Spencer Kellogg | 191.3 | 191.3 | 191.3 |
| Mineral Spirits 663 | Aliphatic Hydrocarbon | Union Oil Company of California | 46.8 | 46.8 | 46.8 |
| Paint Drier | 6% Cobalt Naphthenate | Tenneco Chemical, Inc. | 1.8 | 1.8 | 1.8 |
| Paint Drier | 4% Calcium Naphthenate | Tenneco Chemical, Inc. | 8.6 | 8.6 | 8.6 |
| Exkin #2 | Oxime Antiskin Agent | Tenneco Chemical, Inc. | 1.0 | 1.0 | 1.0 |
| MIX AT 3000 RPM ||||||
| Stir-In Thickener | Organophilic Clay | Experimental | — | — | 10.0 |
| | | TOTALS | 1055.1 | 1068.4 | 1065.1 |

TABLE XV(a)

ALIPHATIC SOLVENT BASED PAINT COMPOSITION

| Example No. | | Dispersion (Minutes) ||||||  Viscosity (cps) || Sag (mils) |
|---|---|---|---|---|---|---|---|---|---|---|
| | | 5 | 7 | 9 | 11 | 13 | 15 | 24 hr. | 1 week | |
| 169 | 122.5 M.E. BM2Ht/22.5 M.E. Sodium Phthalate | 0 | 0 | 1 | 2 | 2 | 4 | 1900 | 1760 | 8 |
| 170 | 122.5 M3Ht/22.5 M.E. Sodium Phthalate | 0 | 5 | 5 | 5.5 | 5.5 | 5.5 | 1660 | 1500 | 7 |
| comparative example 17 | 114 M.E. M3Ht | 0 | 5 | 5 | 5 | 5 | 5.5 | 1450 | 1460 | 6 |
| comparative example 18 | 95 M.E. 2M2Ht | 0 | 0 | 0 | 0 | 0 | 0 | 480 | | 3 |

1. BM2Ht = Benzyl Dimethyl Di (Hydrogenated tallow) Ammonium bentonite
2. M3Ht = Methyl Tri (Hydrogenated tallow) Ammonium bentonite
3. 2M2Ht = Dimethyl Di (hydrogenated tallow) Ammonium bentonite

TABLE XVI

MODERATELY POLAR PAINTS

| INGREDIENTS | GENERIC NAME | MANUFACTURER | LOW SHEAR POST ADDITION (POUNDS) |
|---|---|---|---|
| Toluene | — | — | 119.0 |
| Methyl Ethyl Ketone | — | — | 150.0 |
| 95% 2-Propanol | — | — | 12.5 |
| Isobutyl Acetate | — | — | 292.0 |
| Stir under slow speed using a Cowles dissolver in a 1 gallon paint can. ||||
| Vinyl VAGH resin | Polyvinyl chloride resin | Union Carbide | 140.0 |
| Sift into the solvent mixture under Cowles agitation. Close the can and roll overnight to complete dissolution of the resin. Transfer to a ball mill. ||||
| ONCOR M50 (registered trademarks of NL) | Basic Lead Silicochromate | NL Industries, Inc. | 100.4 |
| Indian Red #5098 | Red Iron Oxide | Pfizer | 9.4 |
| Tricresyl Phosphate | — | Stoney-Mueller | 14.5 |
| Epichlorohydrin | — | — | 1.0 |
| Add to the ball mill and ball mill 16 hr. to a Hegman grind of 5 or better ||||
| Organophilic Clay | | Experimental | 10.0 |
| Mix into finished blank paint using a Cowles dissolver at 3000 rpm for 15 minutes. ||||

TABLE XVI(a)

MODERATELY POLAR SOLVENT BASED PAINT COMPOSITIONS

| Example No. | | Dispersion (Minutes) | | | | | | Viscosity (cps) | | Sag (mils) |
|---|---|---|---|---|---|---|---|---|---|---|
| | | 5 | 7 | 9 | 11 | 13 | 15 | 24 hr. | 1 week | 24 hr. |
| 171 | 122.5 M.E. B2MHt/22.5 M.E. Sodium Oxalate | 0 | 0 | 0 | 0 | 0 | 0 | 2560 | 2720 | 20 |
| 172 | 122.5 M.E. B2MHt/22.5 M.E. Sodium Succinate | 0 | 0 | 0 | 0 | 0 | 0 | 2360 | 2560 | 20 |
| 173 | 122.5 M.E. B2MHt/22.5 M.E. Sodium Citrate | 0 | 0 | 0 | 0 | 0 | 0 | 2340 | 2640 | 20 |
| 174 | 122.5 M.E. B2MHt/22.5 M.E. Sodium Laurate | 0 | 0 | 0 | 4 | 4.5 | 4.5 | 1200 | 1680 | 18 |
| 175 | 122.5 M.E. B2MHt/22.5 M.E. Sodium Oleate | 0 | 0 | 0 | 4.5 | 4.5 | 4.5 | 1500 | 1900 | 20 |
| 176 | 122.5 M.E. B2MHt/22.5 M.E. Sodium Abietate | 0 | 0 | 0 | 0 | 4.5 | 4.5 | 1700 | 2200 | 20 |
| comparative example 19 | 102 B2MHt/Hectorite | 0 | 0 | 0 | 0 | 0 | 0 | 980 | 1180 | 16 |

B2MHt = Dimethyl Hydrogenated tallow Ammonium.

TABLE XVII

ZINC RICH PAINT
(Alcohol Based Formulation)

| INGREDIENTS | GENERIC NAME | MANUFACTURER | CONTROL (POUNDS) | LOW SHEAR PROCESSING (POUNDS) |
|---|---|---|---|---|
| Cellosolve Solvent | 2-Ethoxyethanol | Union Carbide Corp. | 351.1 | 351.1 |
| Ethocel Medium 100 Premium | Ethyl Cellulose | Union Carbide Corp. | 17.8 | 10.6 |
| Sift the Ethocel Medium 100 Premium into the cellosolve solvent while agitating at 6000 rpm with a Cowles Dissolver. Continue mixing for 10 minutes. | | | | |
| M-P-A 1078(X) (registered trademark of NL Industries) | Organic paste dispersed in xylene (registered trademark) | NL Industries, Inc. | 28.5 | — |
| Add and agitate at 6000 rpm for 2 minutes. | | | | |
| Soloid ZN-1 | amorphous, synthetic silica | Union Carbide Corp. | 8.7 | 8.7 |
| L-15 Zinc Dust | fine particle size metallic zinc | Asarco | 1066.0 | 1066.0 |
| Add and agitate at 6000 rpm for 8 minutes. | | | | |
| Ethyl Silicate ESP-X | Tetraethyl orthosilicate binder in Cellosolve Solvent | Union Carbide Corp. | 231.0 | 231.0 |
| Organophilic Clay | | | | 35.7 |
| Mix into the finished paint using a Cowles dissolver at 3000 rpm for 15 minutes | | | | |

TABLE XVII (a)

ZINC RICH PAINT FORMULATIONS
(Alcohol Based Paint Formulations)

| Example No. | Composition | Dispersion after (Min) | | | | | | Viscosity (cps) | | Length Sag (mils) | Settling 24 hr. |
|---|---|---|---|---|---|---|---|---|---|---|---|
| | | 5 | 7 | 9 | 11 | 13 | 15 | 24 hr. | 1 week | | |
| comparative example 20 | Control | 0 | 0 | 0 | 0 | 0 | 0 | 5,100 | 3100 | 10 | 9 |
| comparative example 21 | 122.5 B2MHSAP | 0 | 0 | 0 | 0 | 0 | 1 | 10,820 | 6800 | 35 | 10 |
| 177 | 122.5 B2MHSAP/ 22.5 PA | 0 | 0 | 0 | 0 | 0 | 1 | 12,760 | 9600 | >60 | 10 |

122.5 B2MHSAP = 122.5 M.E. Benzyl Dimethyl 12-Hydroxystearamidopropyl Ammonium Chloride reacted with 100 g of Wyoming bentonite.
122.5 B2MHSAP/22.5 PA = 122.5 M.E. Benzyl Dimethyl 12-Hydroxy stearamidopropyl Ammonium Chloride and 22.5 M.E. of Disodium Phthalate reacted with 100 g of Wyoming bentonite.

The invention being thus described, it will be obvious that the same may be varied in many ways. Such variations are not to be regarded as a departure from the spirit and scope of the invention and all such modifications are intended to be included within the scope of the following claims.

We claim:

1. An organophilic clay gellant comprising:
  (a) a smectite-type clay having a cation exchange capacity of at least 75 milliequivalents per 100 grams of said clay;
  (b) an organic anion in an amount ranging from 5 to 100 milliequivalents per 100 grams of said smectite-type clay, 100% active clay basis; and
  (c) an organic cation containing at least one group having 12 to 22 carbon atoms, said organic cation being present in an amount sufficient to at least satisfy the cation exchange capacity of the smectite-type clay and the cationic activity of the organic anion wherein the cation exchange sites of the smectite-type clay are substituted with the organic cation and wherein substantially all of the formed organic cation-organic anion complex is intercalated with the smectite-type clay.

2. The organophilic clay gellant of claim 1 wherein the organic cation is selected from the group consisting of quaternary ammonium salts, phosphonium salts, sulfonium salts and mixtures thereof containing at least one lineal or branched alkyl group having 12 to 22 carbon atoms.

3. The organophilic clay gellant of claim 1 wherein the organic anion is derived from an organic acid having a $pK_A$ less than about 11.0.

4. The organophilic clay gellant of claim 1 wherein the smectite-type clay is selected from the group consisting of hectorite and sodium bentonite.

5. The organophilic clay gellant of claim 1 wherein the amount of said organic cation is from 80 to 200 milliequivalents per 100 grams of clay, 100% active clay basis.

6. The organophilic clay gellant of claim 1 wherein the amount of said organic cation is from 100 to 160 milliequivalents per 100 grams of clay, 100% active clay basis.

7. The organophilic clay gellant of claim 1 wherein the organic anion is derived from a salt of at least one member selected from the group consisting of organic carboxylic acids, organic sulfonic acids, organic sulfates and organic phosphates.

8. An organophilic clay gellant which comprises: the reaction product of (a) a smectite-type clay having a cation exchange capacity of at least 75 milliequivalents per 100 grams of said clay; (b) an organic anion derived from an organic acid having a $pK_A$ less than about 11.0 in an amount ranging from 5 to 100 milliequivalents per 100 grams of said smectite-type clay, 100% active clay basis; and (c) an organic cationic compound selected from the group consisting of:

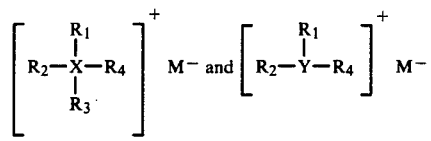

wherein X is nitrogen or phosphorus, Y is sulfur, $M^-$ is selected from the group consisting of chloride, bromide, iodide, nitrite, hydroxyl, acetate, methyl sulfate and mixtures thereof and wherein $R_1$ is an alkyl group containing 12 to 22 carbon atoms; and wherein $R_2$, $R_3$ and $R_4$ are selected from the group consisting of hydrogen, alkyl groups containing 1 to 22 carbon atoms, aryl groups, aralkyl groups containing 1 to 22 carbon atoms on the alkyl chain and mixtures thereof, said organic cationic compound providing organic cation in an amount sufficient to at least satisfy the cation exchange capacity of the smectite-type clay and the cationic activity of the organic anion wherein the cation exchange sites of the smectite-type clay are substituted with the organic cation and wherein substantially all of the formed organic cation-organic anion complex is intercalated with the smectite-type clay.

9. A process for preparing an organophilic clay gellant which comprises:
(a) preparing a slurry of smectite-type clay having a cation exchange capacity of at least 75 milliequivalents per 100 grams of said clay in water at 1 to 80% by weight of said clay;
(b) heating the slurry to a temperature between 20° C. and 100° C.;
(c) adding 5 to 100 milliequivalents of an organic anion per 100 grams of clay, 100% active clay basis and an organic cation containing at least one group having 12 to 22 carbon atoms in an amount sufficient to at least satisfy the cation exchange capacity of the smectite-type clay and the cationic activity of the organic anion while agitating the reaction mixture;
(d) continuing the reaction for a sufficient time to form a reaction product comprising the smectite-type clay having its cation exchange sites substituted with the organic cation and having substantially all of the formed organic cation-organic anion complex intercalated with the smectite-type clay; and
(e) recovering the reaction product.

10. The process of claim 9 wherein the organic cation is selected from the group consisting of quaternary ammonium salts, phosphonium salts and sulfonium salts containing at least one lineal or branched alkyl group having 12 to 22 carbon atoms.

11. The process of claim 9 wherein the organic anion is derived from an organic acid having a $pK_A$ less than about 11.0.

12. The process of claim 9 wherein the smectite-type clay is selected from the group consisting of hectorite and sodium bentonite.

13. The process of claim 9 wherein the amount of said organic anion is from 10 to 50 milliequivalents per 100 grams of said clay, 100% active clay basis.

14. The process of claim 9 wherein the amount of said organic cation is from 80 to 200 milliequivalents per 100 grams of clay, 100% active clay basis.

15. The process of claim 9 wherein the organic anion is added to the smectite-clay prior to the addition of the organic cation.

16. The process of claim 9 wherein the organic anion and organic cation are added to the smectite-type clay in the form of an organic cation-organic anion complex.

17. A process for preparing an organophilic clay gellant which comprises:
(a) preparing a slurry of smectite-type clay having a cation exchange capacity of at least 75 milliequivalents per 100 grams of said clay in water at 2 to 7% by weight of said clay;
(b) heating the slurry to a temperature between 20° C. and 100° C.;
(c) adding an organic cation containing at least one group having 12 to 22 carbon atoms in an amount up to the cation exchange capacity of the smectite-type clay to the clay slurry under agitation to prepare an organophilic clay reaction product;
(d) adding 5 to 100 milliequivalents of an organic anion per 100 grams of clay, 100% active clay basis, with agitation to prepare a homogeneous mixture;
(e) adding additional amounts of an organic cation containing at least one group having 12 to 22 carbon atoms to the homogeneous mixture in an amount sufficient to at least satisfy the available remaining cation exchange capacity of the smectite-type clay and cationic activity of the organic anion while agitating the reaction mixture;
(f) continuing the reaction for a sufficient time to form a reaction product comprising the smectite-type clay having its cation exchange sites substituted with the organic cation and having substantially all of the formed organic cation-organic anion complex intercalated with the smectite-type clay; and (g) recovering the reaction product.

18. A process for preparing an organophilic clay gellant which comprises:
(a) preparing a slurry of smectite-type clay having a cation exchange capacity of at least 75 milliequivalents per 100 grams of said clay in water at 2 to 7% by weight of said clay;
(b) heating the slurry to a temperature between 20° C. and 100° C.;
(c) adding 5 to 100 milliequivalents of an organic anion per 100 grams of clay, 100% active clay basis, with agitation to prepare a homogeneous mixture;
(d) adding an organic cation containing at least one group having 12 to 22 carbon atoms to the homogeneous mixture in an amount sufficient to at least satisfy the cation exchange capacity of the smectite-type clay and the cationic activity of the organic anion while agitating the reaction mixture;
(e) continuing the reaction for a sufficient time to form a reaction product comprising the smectite-type clay having its cation exchange sites substituted with the organic cation and having substantially all of the formed organic cation-organic anion complex intercalated with the smectite-type clay; and
(f) recovering the reaction product.

19. A process for preparing an organophilic clay gellant which comprises:
(a) preparing a slurry of smectite-type clay having a cation exchange capacity of at least 75 milliequivalents per 100 grams of said clay in water at 2 to 7% by weight of said clay;
(b) heating the slurry to a temperature between 20° C. and 100° C.;
(c) adding with agitation an organic cation-organic anion mixture composed of 5 to 100 milliequivalents of the organic anion per 100 grams of clay, 100% active clay basis, and organic cation containing at least one group having 12 to 22 carbon atoms in an amount sufficient to at least satisfy the cation exchange capacity of the smectite-type clay and the cationic activity of the organic anion;
(d) continuing the reaction for a sufficient time to form a reaction product comprising the smectite-type clay having its cation exchange sites substituted with the organic cation and having substantially all of the formed organic cation-organic anion complex intercalated with the smectite-type clay; and
(e) recovering the reaction product.

20. A thixotropic cross-linkable polyester composition comprising an unsaturated polyester and an unsaturated aromatic monomer having dispersed therein from 0.25 to 10% by weight of an organophilic clay gellant which comprises:
(a) a smectite-type clay having a cation exchange capacity of at least 75 milliequivalents per 100 grams of said clay;
(b) an organic anion in an amount ranging from 5 to 100 milliequivalents per 100 grams of said smectite-type clay, 100% active clay basis; and
(c) an organic cation containing at least one group having 12 to 22 carbon atoms, said organic cation being present in an amount sufficient to at least satisfy the cation exchange capacity of the smectite-type clay and the cationic activity of the organic anion wherein the cation exchange sites of the smectite-type clay are substituted with the organic cation and wherein substantially all of the formed organic cation-organic anion complex is intercalated with the smectite-type clay.

21. The composition of claim 20 wherein the smectite-type clay is selected from the group consisting of hectorite and sodium bentonite.

22. A non-aqueous fluid system which comprises a non-aqueous fluid composition and a self-activating organophilic clay rheological composition useful as an additive for non-aqueous fluid systems which comprises:
(a) a smectite-type clay having a cation exchange capacity of at least 75 milliequivalents per 100 grams of said clay;
(b) an organic anion in an amount ranging from 5 to 100 milliequivalents per 100 grams of said smectite-type clay, 100% active clay basis; and
(c) an organic cation containing at least one group having 12 to 22 carbon atoms, said organic cation being present in an amount sufficient to at least satisfy the cation exchange capacity of the smectite-type clay and the cationic activity of the organic anion wherein the cation exchange sites of the smectite-type clay are substituted with the organic cation and wherein substantially all of the formed organic cation-organic anion complex is intercalated with the smectite-type clay.

23. The non-aqueous fluid system of claim 22 wherein the smectite-type clay is selected from the group consisting of hectorite and sodium bentonite.

24. A non-aqueous fluid system which comprises a non-aqueous fluid composition and an organophilic clay gellant which comprises: the reaction product of (a) a smectite-type clay having a cation exchange capacity of at least 75 milliequivalents per 100 grams of said clay; (b) an organic anion derived from an organic acid having a $pK_A$ less than about 11.0 in an amount ranging from 5 to 100 milliequivalents per 100 grams of said smectite-type clay, 100% active clay basis; and (c) an organic cationic compound selected from the group consisting of:

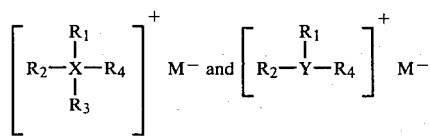

wherein X is nitrogen or phosphorus, Y is sulfur, $M^-$ is selected from the group consisting of chloride, bromide, iodide, nitrite, hydroxyl, acetate, methyl sulfate and mixtures thereof; and wherein $R_1$ is an alkyl group containing 12 to 22 carbon atoms and wherein $R_2$, $R_3$ and $R_4$ are selected from the group consisting of hydrogen, alkyl groups containing 1 to 22 carbon atoms, aryl groups, aralkyl groups containing 1 to 22 carbon atoms on the alkyl chain and mixtures thereof, said organic cationic compound providing organic cation in an amount sufficient to at least satisfy the cation exchange capacity of the smectite-type clay and the cationic activity of the organic anion wherein the cation exchange sites of the smectite-type clay are substituted with the organic cation and wherein substantially all of the formed organic cation-organic anion complex is intercalated with the smectite-type clay.

* * * * *